US008008259B2

(12) United States Patent
Bock et al.

(10) Patent No.: US 8,008,259 B2
(45) Date of Patent: Aug. 30, 2011

(54) NEUROTROPHIN-DERIVED PEPTIDE SEQUENCES

(75) Inventors: Elisabeth Bock, Charlottenlund (DK); Vladimir Berezin, København N (DK)

(73) Assignee: Copenhagen University, Techtrans Unit, Koebenhavn N D (DK)

( * ) Notice: Subject to any disclaimer, the term of this patent is extended or adjusted under 35 U.S.C. 154(b) by 62 days.

(21) Appl. No.: 12/092,919

(22) PCT Filed: Nov. 7, 2006

(86) PCT No.: PCT/DK2006/000612
§ 371 (c)(1),
(2), (4) Date: Nov. 24, 2008

(87) PCT Pub. No.: WO2007/051477
PCT Pub. Date: May 10, 2007

(65) Prior Publication Data
US 2009/0074779 A1    Mar. 19, 2009

(30) Foreign Application Priority Data

Nov. 7, 2005  (DK) ................................. 2005 01538

(51) Int. Cl.
*A61K 38/08*  (2006.01)
*A61K 38/10*  (2006.01)
*A61K 38/16*  (2006.01)

(52) U.S. Cl. ...................... 514/17.7; 514/21.4; 514/21.5; 514/21.6

(58) Field of Classification Search .......................... None
See application file for complete search history.

(56) References Cited

U.S. PATENT DOCUMENTS

| 6,723,344 | B2 * | 4/2004 | Sakiyama-Elbert et al. | . 424/484 |
| 2004/0072291 | A1 * | 4/2004 | Carr et al. | .................... 435/69.1 |
| 2005/0048606 | A1 | 3/2005 | Wang et al. | |

FOREIGN PATENT DOCUMENTS

| JP | 06317587 | | 11/1994 |
| WO | WO 92/02620 | | 2/1992 |
| WO | WO 93/25684 | | 12/1993 |
| WO | WO 9954470 A2 | * | 10/1999 |
| WO | WO 02/066514 | | 8/2002 |
| WO | WO 02062832 | * | 8/2002 |
| WO | WO 03/045998 | | 6/2003 |
| WO | WO 2005/019266 | | 3/2005 |

OTHER PUBLICATIONS

Allen & Dawbarn "Clinical relevance of the neurotrophins and their receptors," Clinical Science, 2006, 110, 175-191, especially pp. 175-181.*
Massa et al. "Alzheimer's Therapeutics" J. Mol. Neuro., 2002, 19, 107-11.*
Bibel et al. Neurotrophins: Key regulators of cell fate and cell shape in the vertebrate nervous system. Genes & Development, 2000, 14: 2919-2937.
Bothwell, Mark. p75NTR: A receptor after all. Science, 272: No. 5261 (Apr. 26, 1996) 506-507.
Carter, Bruce D and Lewin, Gary R. Neutotrophins live let die: Does p75NTR decide? Neuron, 18: 187-190, Feb. 1997.
Chao, Moses V. Neurotrophin receptors: A window into neuronal differentiation. Neuron, 9: 583-593, Oct. 1992.
D'Mello et al. Induction of apoptosis in cerebellar granule neurons by low potassium: Inhibition of death by insulin-like growth factor I and cAMP. Proc. Natl. Acad. Sci. USA, vol. 90, 10989-10993, Dec. 1993, Neurobiology.
Hu et al. NGF stimulates extensive neurite outgrowth from implanted dorsal root ganglion neurons following transplantation into the adult rat inner ear. Neurobiology of Disease, 18 (2005) 184-192.
Jakubowska-Dogru, Ewa and Gümüsbas Umut. Chronic intracerebroventricular NGF administration improves memory in young adult memory deficient rats. Neurosci. Letters. 382 (2005) 45-50.
Lee et al. The uniqueness of being a neurotrophin receptor. Current opinion in Neurobiology, 2001, 11:218-286.
Longo et al. Synthetic NGF peptide derivatives prevent neuronal death via a p75 receptor-dependent mechanism. Journal of Neuroscience Research, 48: 1-17 (1997).
Ma et al. Nerve growth factor receptor-mediated gene transfer. Molecular Therapy, vol. 9, No. 2, Feb. 2004, 270-281.
Maliartchouk et al. Genuine monovalent ligands of TrkA nerve growth factor receptors reveal a novel pharmacological mechanism of action. The Journal of Biological Chemistry, vol. 275, No. 14, Apr. 7, 9946-9956, 2000.
O'Leary, Paul D. and Hughes, Richard A. Design of potent peptide mimetics of brain-derived neurotrophic factor. The Journal of Biological Chemistry, vol. 278, No. 28, Jul. 11, 25738-25744, 2003.
Penkowa et al. Astrocyte-targeted expression of IL-6 protects the CNS against a focal brain injury. Experimental Neurology, 181 (2003) 130-148.
Rønn et al. A simple procedure of quantification of neurite outgrowth based on stereological principles. Journal of Neuroscience Methods, 100 (2000) 25-32.
Salehi et al. Alzheimer's disease and NGF signaling. Journal of Neural Transmission (2004) 111: 323-345.
Shoval, Gal and Weizman, Abraham. The possible role of neurotrophins in the pathogenesis and therapy of schizophrenia. European Neuropsychopharmacology, 15 (2005) 319-329.
Thomas, Kerrie and Davies, Alun. Neurotrophins: A ticket to ride for BDNF. Current Biology, vol. 15, No. 7, 2005, R262-R264.
Tuszynski et al. A phase 1 clinical trial of nerve growth factor gene therapy for alzheimer disease. Nature Medicine, vol. 11, No. 5, May 2005, 551-555.

(Continued)

Primary Examiner — Christina Bradley
(74) Attorney, Agent, or Firm — Iver P. Cooper

(57) ABSTRACT

The present invention relates to peptide sequences capable of stimulating neuronal cell differentiation, neural cell survival and neuronal plasticity associated with memory and learning. The peptide sequences of the invention are derived from the proteins belonging to neurotrophic factors, such as NGF, NT3, NT4/5 and BDNF. The invention also relates to pharmaceutical compositions comprising said peptide fragments and uses thereof for treatment of a disease or condition wherein the effects of stimulating neuronal cell differentiation, neuronal cell survival, stimulating neural plasticity associated with learning and memory are beneficial for treatment.

43 Claims, 5 Drawing Sheets

OTHER PUBLICATIONS

Ullrich, Axel and Schlessinger, Joseph. Signal transduction by receptors with tyrosine kinase activity. Cell, vol. 61, 203-212, Apr. 20, 1990.

Walz et al. Short- and long-term memory are differentialy modulated by hippocampal nerve growth factor and fibroblast growth factor. Neurochemical Research, vol. 30, No. 2, Feb. 2005, 185-190.

Williams et al. Overcoming the inhibitors of myelin with a novel neurotrophin strategy. The Journal of Biological Chemistry, vol. 280, No. 7, Feb. 18, 5862-5869, 2005.

Xie et al. Nerve growth factor (NGF) loop 4 mimetics activate ERK and AKT and promote NGF-like neurotrophic effects. The Journal of Biological Chemistry, vol. 275, No. 38, Sep. 22, 29868-29874, 2000.

* cited by examiner

SEQUENCE LISTING

<160> NUMBER OF SEQ ID NOS: 26

<210> SEQ ID NO 1
<211> LENGTH: 14
<212> TYPE: PRT
<213> ORGANISM: Homo sapiens

<400> SEQUENCE: 1

Tyr Glu Thr Lys Cys Arg Asp Pro Asn Pro Val Asp Ser Gly
1               5                   10

<210> SEQ ID NO 2
<211> LENGTH: 14
<212> TYPE: PRT
<213> ORGANISM: Homo sapiens

<400> SEQUENCE: 2

Phe Glu Thr Arg Cys Lys Glu Ala Arg Pro Val Lys Asn Gly
1               5                   10

<210> SEQ ID NO 3
<211> LENGTH: 18
<212> TYPE: PRT
<213> ORGANISM: Homo sapiens

<400> SEQUENCE: 3

```
Tyr Glu Thr Arg Cys Lys Ala Asp Asn Ala Glu Gly Gly Pro Gly
1               5                   10                  15

Ala Gly

<210> SEQ ID NO 4
<211> LENGTH: 14
<212> TYPE: PRT
<213> ORGANISM: Homo sapiens

<400> SEQUENCE: 4

Phe Glu Thr Lys Cys Asn Pro Met Gly Tyr Thr Lys Glu Gly
1               5                   10

<210> SEQ ID NO 5
<211> LENGTH: 7
<212> TYPE: PRT
<213> ORGANISM: Homo sapiens

<400> SEQUENCE: 5

Arg Ile Asp Thr Ala Cys Val
1               5

<210> SEQ ID NO 6
<211> LENGTH: 7
<212> TYPE: PRT
<213> ORGANISM: Homo sapiens

<400> SEQUENCE: 6

Arg Ile Asp Thr Ser Cys Val
1               5

<210> SEQ ID NO 7
<211> LENGTH: 11
<212> TYPE: PRT
<213> ORGANISM: Homo sapiens

<400> SEQUENCE: 7

Cys Val Leu Ser Arg Lys Ala Val Arg Arg Ala
1               5                   10

<210> SEQ ID NO 8
<211> LENGTH: 10
<212> TYPE: PRT
<213> ORGANISM: Homo sapiens

<400> SEQUENCE: 8

Cys Ala Leu Ser Arg Lys Ile Gly Arg Thr
1               5                   10

<210> SEQ ID NO 9
<211> LENGTH: 11
<212> TYPE: PRT
<213> ORGANISM: Homo sapiens

<400> SEQUENCE: 9

Val Cys Thr Leu Leu Ser Arg Thr Gly Arg Ala
1               5                   10

<210> SEQ ID NO 10
<211> LENGTH: 10
<212> TYPE: PRT
<213> ORGANISM: Homo sapiens

<400> SEQUENCE: 10

Val Cys Thr Leu Thr Ile Lys Arg Gly Arg
```

```
<210> SEQ ID NO 11
<211> LENGTH: 12
<212> TYPE: PRT
<213> ORGANISM: Homo sapiens

<400> SEQUENCE: 11

Ser Ser His Pro Ile Phe His Arg Gly Glu Phe Ser
1               5                   10

<210> SEQ ID NO 12
<211> LENGTH: 12
<212> TYPE: PRT
<213> ORGANISM: Homo sapiens

<400> SEQUENCE: 12

Tyr Ala Glu His Lys Ser His Arg Gly Glu Tyr Ser
1               5                   10

<210> SEQ ID NO 13
<211> LENGTH: 13
<212> TYPE: PRT
<213> ORGANISM: Homo sapiens

<400> SEQUENCE: 13

Ser Glu Thr Ala Pro Ala Ser Arg Arg Gly Glu Leu Ala
1               5                   10

<210> SEQ ID NO 14
<211> LENGTH: 11
<212> TYPE: PRT
<213> ORGANISM: Homo sapiens

<400> SEQUENCE: 14

His Ser Asp Pro Ala Arg Arg Gly Glu Leu Ser
1               5                   10

<210> SEQ ID NO 15
<211> LENGTH: 16
<212> TYPE: PRT
<213> ORGANISM: Homo sapiens

<400> SEQUENCE: 15

Thr Phe Val Lys Ala Leu Thr Met Asp Gly Lys Gln Ala Ala Trp Arg
1               5                   10                  15

<210> SEQ ID NO 16
<211> LENGTH: 17
<212> TYPE: PRT
<213> ORGANISM: Homo sapiens

<400> SEQUENCE: 16

Thr Tyr Val Arg Ala Leu Thr Ser Glu Asn Asn Lys Leu Val Gly Trp
1               5                   10                  15

Arg

<210> SEQ ID NO 17
<211> LENGTH: 17
<212> TYPE: PRT
<213> ORGANISM: Homo sapiens

<400> SEQUENCE: 17

Ser Tyr Val Arg Ala Leu Thr Ala Asp Ala Gln Gly Arg Val Gly Trp
1               5                   10                  15
```

Arg

<210> SEQ ID NO 18
<211> LENGTH: 17
<212> TYPE: PRT
<213> ORGANISM: Homo sapiens

<400> SEQUENCE: 18

Ser Tyr Val Arg Ala Leu Thr Met Asp Ser Lys Lys Arg Ile Gly Trp
1               5                   10                  15

Arg

<210> SEQ ID NO 19
<211> LENGTH: 11
<212> TYPE: PRT
<213> ORGANISM: Homo sapiens

<400> SEQUENCE: 19

Arg Gly Ile Asp Ser Lys His Trp Asn Ser Tyr
1               5                   10

<210> SEQ ID NO 20
<211> LENGTH: 16
<212> TYPE: PRT
<213> ORGANISM: Homo sapiens

<400> SEQUENCE: 20

Arg Gly Ile Asp Asp Lys His Trp Asn Ser Gln Cys Lys Thr Ser Gln
1               5                   10                  15

<210> SEQ ID NO 21
<211> LENGTH: 11
<212> TYPE: PRT
<213> ORGANISM: Homo sapiens

<400> SEQUENCE: 21

Arg Gly Val Asp Arg Arg His Trp Val Ser Glu
1               5                   10

<210> SEQ ID NO 22
<211> LENGTH: 11
<212> TYPE: PRT
<213> ORGANISM: Homo sapiens

<400> SEQUENCE: 22

Arg Gly Ile Asp Lys Arg His Trp Asn Ser Gln
1               5                   10

<210> SEQ ID NO 23
<211> LENGTH: 18
<212> TYPE: PRT
<213> ORGANISM: Homo sapiens

<400> SEQUENCE: 23

Arg Ile Asp Thr Ala Cys Val Cys Val Leu Ser Arg Lys Ala Val Arg
1               5                   10                  15

Arg Ala

<210> SEQ ID NO 24
<211> LENGTH: 17
<212> TYPE: PRT
<213> ORGANISM: Homo sapiens

<400> SEQUENCE: 24

```
Arg Ile Asp Thr Ser Cys Val Cys Ala Leu Ser Arg Lys Ile Gly Arg
1               5                   10                  15

Thr

<210> SEQ ID NO 25
<211> LENGTH: 17
<212> TYPE: PRT
<213> ORGANISM: Homo sapiens

<400> SEQUENCE: 25

Arg Ile Asp Thr Ala Cys Val Cys Thr Leu Leu Ser Arg Thr Gly Arg
1               5                   10                  15

Ala

<210> SEQ ID NO 26
<211> LENGTH: 16
<212> TYPE: PRT
<213> ORGANISM: Homo sapiens

<400> SEQUENCE: 26

Arg Ile Asp Thr Ser Cys Val Cys Thr Leu Thr Ile Lys Arg Gly Arg
1               5                   10                  15
```

NEUROTROPHIN-DERIVED PEPTIDE SEQUENCES

FIELD OF THE INVENTION

The present invention relates to peptide sequences capable of stimulating neuronal cell differentiation, neural cell survival and neuronal plasticity associated with memory and learning. The peptide sequences of the invention are derived from the proteins belonging to neurotrophic factors, such as NGF, NT3, NT4/5 and BDNF. The invention also relates to pharmaceutical compositions comprising said peptide fragments and uses thereof for treatment of a disease or condition wherein the effects of stimulating neuronal cell differentiation, neuronal cell survival, stimulating neural plasticity associated with learning and memory are beneficial for treatment.

BACKGROUND OF THE INVENTION

The growth, maintenance and regeneration of neurons is regulated at least in part by certain polypeptide growth factors, known as neuroptrophins (NTs), which bind to and activate cell surface receptors of the Trk family having an intrinsic tyrosine kinase activity. Upon neurotrophin binding, these receptors are believed become autophosphorylated on one or more amino acid residues and subsequently associate with intracellular molecules important for signal transduction (For a review, see Ulrich & Schlessinger, Cell 1990, 61:203-212; Chao, Neuron 1992, 9:583-593)

Neurotrophins are small (approx. 13 kDa) highly basic dimeric proteins that profoundly affect the development of the nervous system in all vertebrates' species.

Nerve growth factor (NGF) is the first and best characterized member of the neurotrophin family. It exists within the CNS as a homodimer, and its gene is located on chromosome 1 (p21-p22.1 region). NGF was shown to promote survival of primary sensory neurons, and sympathetic and cholinergic neurons of the basal forebrain. It has also been demonstrated that NGF is a protection factor against axotomy-induced neurodegeneration and age-related atrophy. It has been suggested that NGF plays a role in pathophysiology and pharmacotherapy of neurodegenerative disorders such as Alzheimer's disease. In addition, it was shown to significantly decrease neurodegeneration in hippocampal neurons exposed to glutamate at toxic concentrations and preserve cell morphology (reviewed by Salehi et al., 2004; Tuszynski M H, et al. Nat. Med. 2005 June; 11(6):551-5; Jakubowska-Dogru E, Gumusbas U Neurosci Lett. 2005 Jul. 1; 382(1-2):45-50; Walz R, et al Neurochem Res. 2005 February; 30(2):185-90; Hu Z et al. Neurobiol Dis. 2005 February; 18(1):184-92).

Brain-derived neurotrophic factor (BDNF) is another well-characterised member of the neurotrophin family. The BDNF gene is located on chromosome 11, band p13. The structure of BDNF protein is similar with the structure of NGF. BDNF is more widespread in the CNS than NGF. Like NGF, BDNF is abundant in the hippocampus, brain region which maintains high degree of neural plasticity in adult brain, which essentially associated with learning and memory. It is noteworthy that the regulation of expression of both NGF and BDNF within the hippocampus is, at least partly, controlled by the cholinergic and glutamatergic systems. Hippocampal damage has been shown to lead to up-regulation of BDNF expression. In addition, BDNF, similarly to NGF, acts as a survival factor for primary sensory and cholinergic neurons of the basal forebrain. Further, BDNF was found to promote survival of a wide range of other neuronal cell types, e.g. dopaminergic neurons of the substania nigra, cerebellar granule neurons, motoneurons, neurons of the locus ceruleus and retinal ganglion cells, in which NGF does not seem to play a vital role.

Neurotrophin-3 (NT-3) has a highly similar structure to both NGF and BDNF, however, the expression of this growth factor in the nervous system is somewhat different from NGF or BDNF. In contrast to NGF and BDNF the level of NT-3 in the CNS is high during foetal development and in newborn brain and it is reduced in the adult brain. NT-3 level in the hippocampus of newborn animals is significantly higher than the level of other neurotrophins. Based on these findings it was proposed that NT-3 plays a central role in early neuronal development and malfunction of this neurotrophin during development of the brain may lead to hippocampal pathologies such as schizophrenia. Like NGF and BDNF, NT-3 prolongs survival of primary sensory neurons, in particular cells of the neural crest, and it enhances dopaminergic neurons survival (for review see Shoval and Weizman, 2005).

The fourth described member of the neurtophin growth factor family is neurotrophin 4/5 (NT-4/5). NT-4/5 is as all the other neurotrophins a potent survival factor for neuronal cells, in particular it has been shown to promote survival sensory neurons of the neural crest and placodes, motoneurons, neurons of the basal forebrain and locus ceruleus. It also serves as a differentiation factor for basal forebrain neurons and motoneurons. It is involved in the promotion of nerve regeneration and synaptic activity of hippocampal neurons (for review see Shoval and Weizman, 2005).

Nerve growth factor receptor (NGFR), also referred to as $p^{75NTR}$ due to its molecular mass, is the ubiquitous receptor for all neutrophins. At the time of its discovery, NGFR was considered a unique type of protein. Subsequently, however, a large superfamily of tumor necrosis factor receptors were found to share the overall structure of NGFR (4 extracellular ligand-binding, cysteine-rich repeats, or CRs, and signaling through association with, or disassociation from, cytoplasmic interactors). The identification of this superfamily helped elucidate some of the biologic functions of NGFR, including its ultimate involvement in the nuclear factor kappa-B and apoptosis pathways. NGFR/$p^{75NTR}$ is primarily associated with cell death. As a monomer, NGFR binds all NTs with low affinity. Higher affinity binding of NTs is achieved by association the factors with higher molecular mass receptors of the tropomyosin receptor kinases family (TRK family), TRKA (NTRK1), TRKB (NTRK2), and TRKC (NTRK3). TRKA, TRKB, and TRKC are specific for NGF, NT-4/5 and BDNF, and NT-3, respectively. NT-3 also binds to TRKA and TRKB, but with significantly lower affinity (for review NTs and its receptors see Bothwell, Science 272: 506-507, 1996, Carter and Lewin, Neuron 18: 187-190, 1997, Bibel and Barde, Genes Dev. 14: 2919-2937, 2000).

Binding NTs to their receptors and regulation of this binding is very complex and strongly regulated during development and in the adult. Neurotrophins and their receptors are involved both in regulation of normal function of the nervous system and in pathology. It has been long apparent that development new compounds that are capable to enhance and/or inhibit function of neurotrophins and/or activity of their receptors would be beneficial in terms of development of new medicine for treatment of a huge number of neural system related diseases. However, despite this long felt need, such compounds have been elusive at best. As large-molecules, the therapeutic delivery of effective levels of neurotrophins themselves presents considerable, possibly insurmountable, challenges. Moreover, natural neurotrophins may interact with other receptors, such as the p75 receptor in neurons, which is associated with neuronal apoptosis and growth cone collapse. However, previous efforts to design peptidomimetic agonists and/or antagonists of Trk-receptors have also been unsuccessful. For example, cyclic peptides derived from loop 1 of the neurotrophin NGF have been reported to moderately mimic the survival activity of NGF. However, these peptides appear to function in a p75, rather Trk-receptor, dependent manner (Long et al., J. Neurosci. Res. 1997, 48:1-17). Some NGF loop 4 cyclic peptides are said to show NGF-like survival activity that is blocked by a Trk antagonist. However, the maximal survival response induced by those peptides is reported to be only 10-15% of the maximal response promoted by the NGF neurotrophin itself (Xie et al., J. Biol. Chem. 2000, 275: 29868-29874; Maliartchouk et al., J. Biol. Chem. 2000, 275: 9946-9956).

Bicyclic and tricyclic dimeric versions of BDNF loop 2 peptides have been shown to have BDNF-like activity. Again, however, the maximal survival response they induce is reported to be only 30% of the maximal response promoted by the natural neurotrophin. (O'Leary et al., J. Biol. Chem. 2003, 278:25738-25744). There continues to exist, therefore, a long felt need for compositions that can modulate (i.e., increase or inhibit) neuronal growth and recovery. There also exists a need for processes and methods (including therapeutic methods) that effectively modulate neuronal growth and recovery.

REFERENCES

Bibel, M.; Barde, Y.-A. *Genes Dev.* 14: 2919-2937, 2000.
Bothwell, M. *Science* 272: 506-507, 1996
Chao, Neuron 1992, 9:583-593
Carter, B. D.; Lewin, G. R.: *Neuron* 18:187-190, 1997.
D'Mello S. R., Galli C., Ciotti T. and Calissano P. Proc. Natl Acad. Sci. USA, 1993, 90:10 989-10 993.
Jakubowska-Dogru E, Gumusbas U Neurosci Lett. 2005 Jul. 1; 382(1-2):45-50
Hu Z et al. Neurobiol Dis. 2005 February; 18(1):184-92
Lee et al., Curr. Opin. Neurobiol. 2001, 11: 281-286
Long et al., J. Neurosci. Res. 1997, 48: 1-17
Maliartchouk et al., J. Biol. Chem. 2000, 275: 9946-9956
O'Leary et al., J. Biol. Chem. 2003, 278:25738-25744
Penkowa M, Giralt M, Lago N, Camats J, Carrasco J, Hernandez J, Molinero A, Campbell I L, Hidalgo J. Exp Neurol. 2003, 181:1301-48.
Rønn L C, Ralets I, Hartz B P, Bech M, Berezin A, Berezin V, Moller A, Bock E. J. Neurosci. Methods, 2000, 100:25-32.
Salehi A, Delcroix J D, Swaab D F. J Neural Transm. 2004, 111:323-45.
Shoval G and Weizman A. Eur. Neuropsychopharm. 2005, 15:319-329.
Thomas K and Davies A. Curr. Biol. 2005, 15:R262-R264.
Tuszynski M H, et al. Nat. Med. 2005 June; 11(6):551-5)
Ulrich & Schlessinger, Cell 1990, 61:203-212
Walz R, et al Neurochem Res. 2005 February; 30(2):185-90
Xie et al., J. Biol. Chem. 2000, 275: 29868-29874

SUMMARY OF THE INVENTION

The present invention relates to short peptide sequences derived from neutrophins which are very potent at stimulating neuronal cell differentiation, neuronal cell survival and neural plasticity associated with learning and memory mediated by neutrophin receptors. According to the invention, the peptide sequences comprise one or more common amino acid motifs which are important for biological activity of the peptides Thus, in the first aspect, the present invention relates to an isolated peptide sequence comprising 5 to 25 contiguous amino acid residues, comprising the amino acid motif $x_{p1}$-D/E-T-$x^{B1}$-C (motif I)

wherein
$x^{p1}$ is a hydrophobic amino acid residue, and
$x^{a1}$ is K, R, S, A.

In another aspect of the invention, a peptide sequence comprising motif (i) may further comprise either/both motif (II) $x^{p2}$-$(x^a)_1$-$(x_a)_2$-$x^{+/-}$-$x^{a2}$-G or/and motif (III) R/K/A/G-L/V/I-T/D-$x^{a2}$-$x^{+/-}$ wherein
$x^{p2}$ is a hydrophobic or basic amino acid residue,
$(x^a)$ is any amino acid residue or a bond,
$x^{+/-}$ is a charged amino acid residue, and
$x^{a2}$ is any amino acid residue, The invention discloses particular peptide sequences derived from NGF, NT3, NT4/5 and BDNF which comprise at least one of the motifs of the above and are capable of stimulating neuronal cell differentiation, neuronal cell survival and/or neural plasticity associated with learning and memory.

Further, the invention relates to a compound comprising a peptide sequence comprising at least one of the motifs of above, in particular a compound comprising a sequence derived from NGF, NT3, NT4/5 or BDNF.

The invention also relates to uses of the peptide sequences and compounds comprising thereof for the manufacture of a medicament and/or for the production of an antibody. The invention also relates to pharmaceutical compositions comprising peptides, compounds and/or antibodies of the invention.

Methods of stimulating of neurite cell differentiation, neuronal cell survival and/or neuronal plasticity associated with learning and memory comprising using peptides, compounds, antibodies and/or pharmaceutical compositions of the invention are also in the scope of the protection, as well as methods of treatment comprising administering to an individual in need an effective amount of a peptide, compound, antibody or pharmaceutical composition of the invention.

DETAILED DESCRIPTION OF THE INVENTION

I Peptide Sequences

Figure 1:
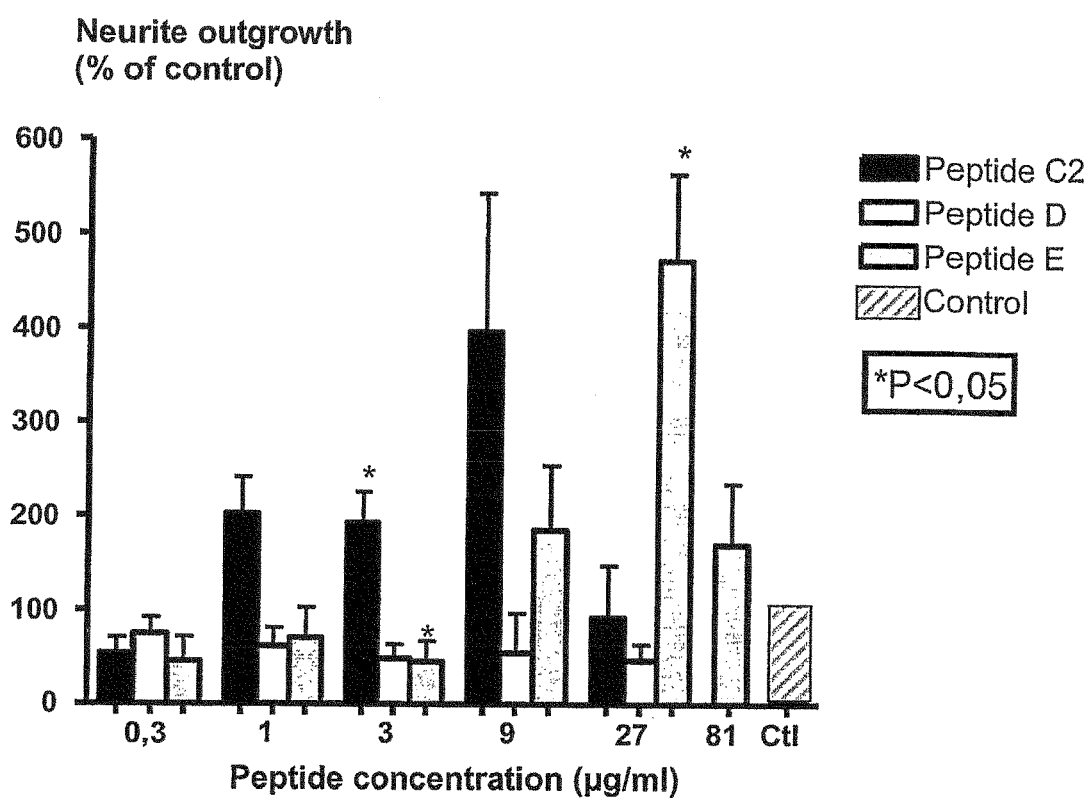
FIG. 1 demonstrates the effect of NGF-derived peptides, NGF-C2, NGF-D and NGF-E, on neurite outgrowth from cerebella granular neurons (CGN).
Figure 2:
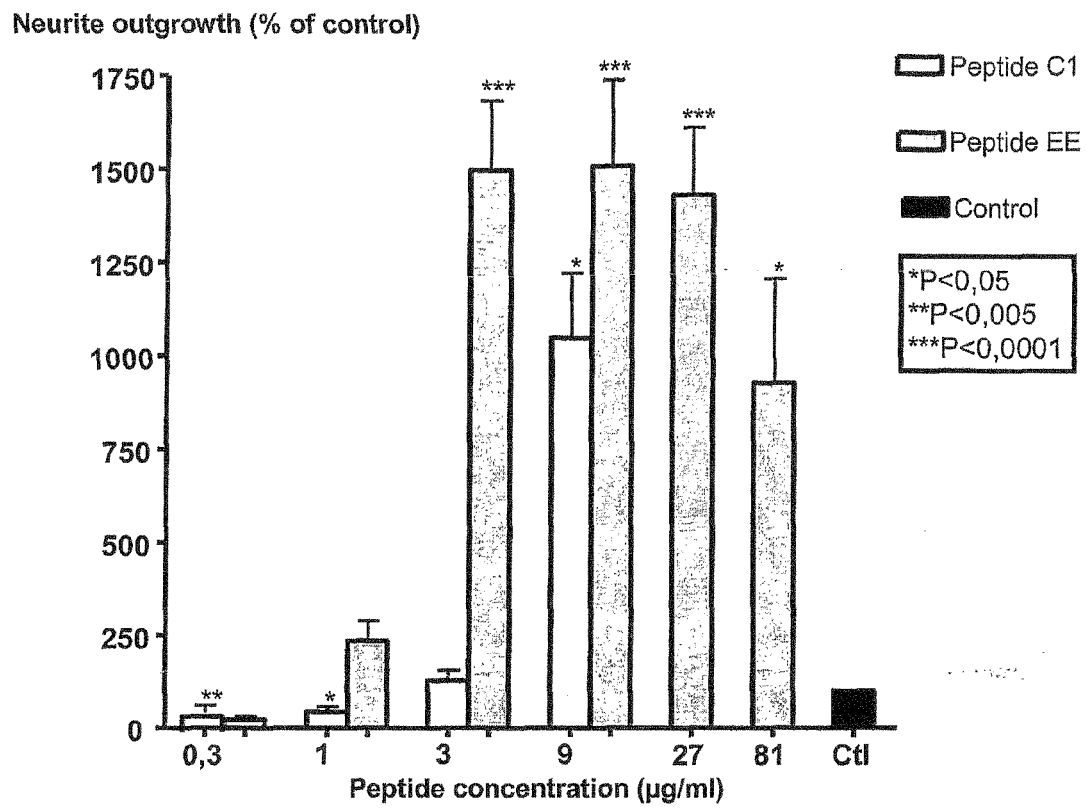
FIG. 2 demonstrates the effect of NGF-derived peptides, NGF-C1 and NGF-EE, on neurite outgrowth from CGN.

One aspect of the invention relates to a peptide sequence comprising 5 to 25 contiguous amino acid residues, comprising the amino acid motif (motif I)

$$x^{p1}\text{-D/E-T-}x^{a1}\text{-C}$$

wherein
$x^{p1}$ is a hydrophobic amino acid residue, and
$x^{a1}$ is K, R, S or A.

The $x^{p1}$ residue of motif (I) according to the invention may be any hydrophobic residue, however, in a preferred embodiment $x^{p1}$ is selected from Y, F or I. Thus, in one preferred embodiment it may be Y, in another F and still another preferred embodiment it may be I.

The peptide sequence of the invention comprising the motif of above may further comprise another amino acid motif $x^{p2}$-$(x^a)_1$-$(x^a)_2$-$x^{+/-}$-$x^{a2}$-G (motif II), wherein
$x^{p2}$ is a hydrophobic or basic amino acid residue,
$(x^a)$ is any amino acid residue or a bond,
$x^{+/-}$ is a charged amino acid residue, and
$x^{a2}$ is any amino acid residue.

Thus, another aspect the invention relates to a peptide sequence of the following formula which comprises both motif (I) and motif (II):

$$x_1\text{-}x^{p1}\text{-D/E-T-}x^{a1}\text{-C-}(x)_n\text{-}x^{p2}\text{-}(x^a)\text{-}(x^a)\text{-}x^{+/-}\text{-}x^{a2}\text{-G-}(x)_n$$

wherein
$x_1$ is any amino acid residue
$(x)_n$ is a bond or a sequence of any amino acid residues, wherein n is an integer from 1 to 5, and
$x^{p1}$, $x^{p2}$, $x^{a1}$, $x^{a2}$, $(x^a)$, $x^{+/-}$ are as defined in claims 1-9,
according to the invention $x^{p2}$ of motif (II) may be any hydrophobic amino acid residue, however it is preferred that $x^{p2}$ is selected from A, L, P or Y. In another embodiment $x^{p2}$ may be a charged amino acid residue, in a preferred embodiment a positively charged residue, for example K, R or H. Most preferred positively charged residue according to the invention is K.

The residue of position $(x^a)$ of motif (II) is according to the invention any amino acid residue, however some amino acid residues may be preferred in this position, such preferred amino acid residues may be selected from A, E, F, I, L, R, S, T or V. In some embodiments at least one of the amino aid residues in positions $(x^a)$ may be absent and thus the motif (II) according to the invention may comprise 5 or 4 amino acid residues. In such embodiments the invention relates to an amino acid sequence which comprise motif $x^{p2}$-$(x^a)$-$x^{+/-}$-$x^{a2}$-G comprising one peptide bond in one of the positions $(x^a)$, or the invention relates to an amino acid sequence which comprises motif $x^{p2}$-$x^{+/-}$-$x^{a2}$-G wherein both residues $(x^a)$ are substituted for peptide bonds. In some embodiments it may be preferred that one of the $(x^a)$ residues absent, in other embodiments it may be preferred that both $(x^a)$ are substituted for peptide bonds.

According to the invention $x^{a2}$ may be selected from amino acid residues A, E, G, I, N, R, S or T, and $x^{+/-}$ may be selected from D, E, K, R or H.

Furthermore, the amino acid sequence of above according to the invention may further comprise amino acid motif R/K-A/G-L/V/I-T/D-$x^{B3}$-$x^{+/-}$ (motif III)

wherein
$x^{a3}$ is any amino acid residue, and
$x^{+/-}$ is a charged amino acid residue.

In motif (III) the $x^{a3}$ residue may be selected from A, D, M, R or S, and $x^{+/-}$ is selected from D, E, K, R or H.

Accordingly, another aspect of the invention relates to a peptide sequence of at least 15 contiguous amino acid residues which comprises all three of the above motifs. Such amino acid sequence may according to invention be defined by the following formula:

$$x_1\text{-}x^{p1}\text{-D/E-T-}x^{a1}\text{-C-}(x)_n\text{-}x^{p2}\text{-}(x^a)_1\text{-}(x^a)_2\text{-}x^{+/-}\text{-}x^{a2}\text{-G-}(x)_n\text{-R/K-A/G-L/V/I-T/D-}x^{a3}\text{-}x^{+/-}\text{-}(x)_n$$

wherein
$x_1$, $x^{p1}$, $x^{p2}$, $x^{a1}$, $x^{a2}$, $x^{a3}$ $(x^a)$, $x^{+/-}$ and $(x)_n$ are as discussed above, or a fragment of said sequence comprising at least 5 amino acid residues comprising one of the following motifs:
$x^{p1}$-D/E-T-$x^{a1}$-C (motif I),
$x^{p2}$-$(x^a)_1$-$(x^a)_2$-$x^{+/-}$-$x^{a2}$-G (motif II) or
R/K-A/G-L/V/I-T/D-$x^{a3}$-$x^{+/-}$) (motif III),
wherein $x^{p1}$, $x^{p2}$, $x^{a1}$, $x^{a2}$, $x^{a3}$ $(x^a)$, $x^{+/-}$ are as defined in claims 1 to 14.

The peptide sequence of above may for example comprise a sequence selected from the following sequences:

| Sequence | |
|---|---|
| YETKCRDPNPVDSG | (SEQ ID NO: 1) |
| FETRCKEARPVKNG | (SEQ ID NO: 2) |
| YETRCKADNAEEGGPGAG | (SEQ ID NO: 3) |
| FETKCNPMGYTKEG | (SEQ ID NO: 4) |
| RIDTACV | (SEQ ID NO: 5) |
| RIDTSCV | (SEQ ID NO: 6) |
| CVLSRKAVRRA | (SEQ ID NO: 7) |
| CALSRKIGRT | (SEQ ID NO: 8) |
| VCTLLSRTGRA | (SEQ ID NO: 9) |
| VCTLTIKRGR | (SEQ ID NO: 10) |
| SSHPIFHRGEFS | (SEQ ID NO: 11) |
| YAEHKSHRGEYS | (SEQ ID NO: 12) |
| SETAPASRRGELA | (SEQ ID NO: 13) |
| HSDPARRGELS | (SEQ ID NO: 14) |
| TFVKALTMDGKQAAWR | (SEQ ID NO: 15) |
| TYVRALTSENNKLVGWR | (SEQ ID NO: 16) |
| SYVRALTADAQGRVGWR | (SEQ ID NO: 17) |
| SYVRALTMDSKKRIGWR | (SEQ ID NO: 18) |
| RGIDSKHWNSY | (SEQ ID NO: 19) |
| RGIDDKHWNSQCKTSQ | (SEQ ID NO: 20) |
| RGVDRRHWVSE | (SEQ ID NO: 21) |
| RGIDKRHWNSQ | (SEQ ID NO: 22) |
| RIDTACVCVLSRKAVRRA | (SEQ ID NO: 23) |
| RIDTSCVCALSRKIGRT | (SEQ ID NO: 24) |
| RIDTACVCTLLSRTGRA | (SEQ ID NO: 25) |
| RIDTSCVCTLTIKRGR | (SEQ ID NO: 26) | or a fragment, or a variant or a homologue thereof.

It is understood that all the above sequences SEQ ID NOs: 1-26 comprise at least one of the motifs (I), (II) or (III).

In some embodiments a peptide sequence of the invention may comprise a sequence selected from the sequences identified as SEQ ID NOs: 5-22, such as SEQ ID NO: 5 or 6, or for example a sequence selected from the sequences identified as SEQ ID NOs: 7-10, or a sequence selected from the sequences identified as SEQ ID NOs: 11-14 or SEQ ID NOs: 15-22, for example selected from SEQ ID NOs: 15-18 or SEQ ID NOs: 19-22.

The peptide sequence may also comprise more then one of sequences identified as SEQ ID NOs: 5-22. Such peptide sequence may be for example a sequence selected from the sequences identified as SEQ ID NOs: 1-4, or a sequence selected from the sequence identified as SEQ ID NOs: 23-26.

According to the invention the peptide sequences preferably encompass 5 to 25 amino acid residues. Thus, in one embodiment a preferred peptide sequence may have the length in the range of 5 to 10 amino acid residues, such as 6 to 9 amino acid residues, for example 7 or 8 amino acid residues, or the length of the peptide sequence may be in the range of 11 to 15 amino acid residues, such as for example 12 to 14 amino acid residues, for example 13 amino acid residues. The length of a preferred peptide sequence in another embodiment may be in the range of 16 to 25 amino acid residues, for example 17 to 24 amino acid residues, such as 18-23, for example 19-22, it may also be 20 or 21 amino acid residues. However, in some embodiments the length of the peptide sequence of the invention may be longer then the above mentioned length, for example it may be in the range of 26-50 amino acid residues.

As it is mentioned above the present invention relates to fragments, variants and homologues of the peptide sequences described above, which are defined as the following:
  i) a fragment which is a sequence which has at least 40%, more preferably at least 50%, more preferably at least 60%, more preferably at least 70%, more preferably at least 80%, more preferably at least 90%, more preferably at least 95% of the length of a sequence corresponding to a sequence comprising the motif of the invention, in particular a sequence selected from the sequences of SEQ ID NOs: 1-26. Preferably, the fragment comprises a motif of the invention;
  ii) a variant is an amino acid sequence having at least 60%, more preferably at least 70%, more preferably at least 80%, more preferably at least 90%, more preferably 95% homology to a sequence comprising the motif of the invention, in particular to a sequence selected from the sequences of SEQ ID NOs: 1-26, or it is an amino acid sequence having at least 60%, more preferably at least 70%, more preferably at least 80%, more preferably at least 90%, more preferably 95% positive amino acid matches compared to a sequence comprising a motif of the invention, in particular a sequence of SEQ ID NOS: 1-26. A positive amino acid match is defined herein as an identity or similarity defined by physical and/or chemical properties of the amino acids having the same position in two compared sequences. Preferred positive amino acid matches of the pre-sent invention are K to R, E to D, L to M, Q to E, I to V, I to L, A to S, Y to W, K to Q, S to T, N to S and Q to R. The homology of one amino acid sequence with another amino acid is defined as a percentage of identical amino acids in the two collated sequences. The homology of the sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90. Preferably, the variant comprises a motif of the invention;
  iii) a homologue is an amino acid sequence which has less then 60% but more then 30%, such as 50-59%, for example 55%, such as 40-49%, for example 45%, such as 30-39%, for example 35% homology to a sequence comprising a motif of the invention, in particular a sequence of SEQ ID NOs: 1-26. Preferably, the homologue comprises a motif of the invention.

It is presumed that fragments, variants and homologues as defined above remain at least some biological activity of the original sequences, such for example biological activity of the sequences of SEQ ID NOs:1-26, for example the capability of stimulating neural plasticity associated with neural cell differentiation and/or associated with memory and learning, capability of stimulating of cell survival, for example capability of inhibiting apoptosis or capability of activating a receptor of the Trk family.

All the above described sequences are according to the invention isolated peptide sequences.

By the term "isolated peptide sequence" is meant that the peptide sequence is an individual chemical entity. The isolated peptide sequence may be a natural, synthetic or recombinant peptide sequence or a sequence prepared by means of enzymatic/chemical cleavage of a larger polypeptide/protein. By the term "natural" is meant a peptide sequence which is a part of metabolic system of the body and produced in vivo. By the term "recombinant" is meant a peptide sequence which is produced by a method of recombinant technology. Such sequence may be produced both in vivo and in vitro. By the term "synthetic" is a sequence which is produced by means of chemical synthesis.

According to the invention the isolated peptide sequence may derive from the sequence of a protein. The term "derived" is mean that the isolated peptide sequence has the amino acid sequence which is identical with an internal fragment of the amino acid sequence of a protein which was used as a prototype for making said isolated peptide sequence using any technology known in the art, for example recombinant production or chemical synthesis.

Thus, a peptide sequence of the invention may comprise a sequence derived from the sequence of a protein. In one embodiment the sequence may derive from nerve growth factor (NGF), for example from the sequence of NGF polypeptide identified under SwissProt Acc. No: NP_02497; in another embodiment the sequences may derive from neurotrophin-3 (NT-3), for example from the sequence of NT-3 polypeptide identified under of SwissProt Acc. No: NP_002518; in still another embodiment the sequence may derive from neurotrophin-4/5 (NT-4/5), for example from the sequence of NT-4/5 polypeptide identified under of SwissProt Acc. No:AAAV38176, or it may derive from brain-derived neurotrophic factor (BDNF), for example from the sequence of BDNF polypeptide identified under of SwissProt Acc. No: NP_733928.

In one preferred embodiment the invention concerns a sequence derived from NGF which may be selected from the sequences identified as SEQ ID NOs:1, 5, 7, 11, 15, 19 or 23. In another preferred embodiment the invention relates to a sequence derived from NT3, said sequence being selected from the sequences of SEQ ID NOs:2, 6, 8, 12, 16, 20 or 24. Still in another preferred embodiment, the invention relates to a sequence derived from NT415. Such sequence may be selected from the sequences identified as SEQ ID NOs: 3, 5, 9, 13, 17, 21 or 25. Yet, in another preferred embodiment the invention relates to a sequence derived from the sequence of BDNF. The latter sequence may be selected from the sequences identified as SEQ ID NOs:4, 6, 10, 14. 18, 22 or 26.

In the present application the standard one-letter code for amino acid residues is applied as well as the standard three-letter code. Abbreviations for amino acids are in accordance with the recommendations in the IUPAC-IUB Joint Commission on Biochemical Nomenclature Eur. J. Biochem, 1984, vol. 184, pp 9-37. Throughout the description and claims either the three letter code or the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is understood that the C-terminal amino acid of a peptide of the invention exists as the free carboxylic acid, this may also be specified as "—OH". However, the C-terminal amino acid of a compound of the invention may be the amidated derivative, which is indicated as "—NH$_2$". Where nothing else is stated the N-terminal amino acid of a polypeptide comprise a free amino-group, this may also be specified as "H—".

Where nothing else is specified amino acid can be selected from any amino acid, whether naturally occurring or not, such as alfa amino acids, beta amino acids, and/or gamma amino acids. Accordingly, the group comprises but are not limited to: Ala, Val, Leu, Ile, Pro, Phe, Trp, Met, Gly, Ser, Thr, Cys, Tyr, Asn, Gln, Asp, Glu, Lys, Arg, His Aib, Nal, Sar, Orn, Lysine analogues, DAP, DAPA and 4Hyp.

Also, according to the invention modifications of the compounds/peptides may be performed, such as for example glycosylation and/or acetylation of the amino acids.

Basic amino acid residues are according to invention represented by the residues of amino acids Arg, Lys, and His, acidic amino acid residues—by the residues of amino acids Glu and Asp. Basic and amino acid residues constitute a group of charged amino acid residues. The group of hydrophobic amino acid residues is represented by the residues of amino acids Leu, Ile, Val, Phe, Trp, Tyr, and Met.

In one embodiment variants may be understood as exhibiting amino acid sequences gradually differing from the preferred predetermined sequence, as the number and scope of insertions, deletions and substitutions including conservative substitutions increase. This difference is measured as a reduction in homology between the predetermined sequence and the variant.

In one aspect the term "variant of a peptide sequence" means that the peptides may be modified, for example by substitution of one or more of the amino acid residues. Both L-amino acids and D-amino acids may be used. Other modification may comprise derivatives such as esters, sugars, etc. Examples are methyl and acetyl esters.

In another aspect, variants of the peptide fragments according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (Gly) of said variant, or fragments thereof is substituted with an amino acid selected from the group of amino acids consisting of Ala, Val, Leu, and Ile, and independently thereof, variants, or fragments thereof, wherein at least one alanine (Ala) of said variants, or fragments thereof is substituted with an amino acid selected from the group of amino acids consisting of Gly, Val, Leu, and Ile, and independently thereof, variants, or fragments thereof, wherein at least one valine (Val) of said variant, or fragments thereof is substituted with an amino acid selected from the group of amino acids consisting of Gly, Ala, Leu, and Ile, and independently thereof, variants, or fragments thereof, wherein at least one leucine (Leu) of said variant, or fragments thereof is substituted with an amino acid selected from the group of amino acids consisting of Gly, Ala, Val, and Ile, and independently thereof, variants, or fragments thereof, wherein at least one isoleucine (Ile) of said variants, or fragments thereof is substituted with an amino acid selected from the group of amino acids consisting of Gly, Ala, Val and Leu, and independently thereof, variants, or fragments thereof wherein at least one aspartic acids (Asp) of said variant, or fragments thereof is substituted with an amino acid selected from the group of amino acids consisting of Glu, Asn, and Gln, and independently thereof, variants, or fragments thereof, wherein at least one aspargine (Asn) of said variants, or fragments thereof is substituted with an amino acid selected from the group of amino acids consisting of Asp, Glu, and Gln, and independently thereof, variants, or fragments thereof, wherein at least one glutamine (Gln) of said variants, or fragments thereof is substituted with an amino acid selected from the group of amino acids consisting of Asp, Glu, and Asn, and wherein at least one phenylalanine (Phe) of said variants, or fragments thereof is substituted with an amino acid selected from the group of amino acids consisting of Tyr, Trp, His, Pro, and preferably selected from the group of amino acids consisting of Tyr and Trp, and independently thereof, variants, or fragments thereof, wherein at least one tyrosine (Tyr) of said variants, or fragments thereof is substituted with an amino acid selected from the group of amino acids consisting of Phe, Trp, His, Pro, preferably an amino acid selected from the group of amino acids consisting of Phe and Trp, and independently thereof, variants, or fragments thereof, wherein at least one arginine (Arg) of said fragment is substituted with an amino acid selected from the group of amino acids consisting of Lys and His, and independently thereof, variants, or fragments thereof, wherein at least one lysine (Lys) of said variants, or fragments thereof is substituted with an amino acid selected from the group of amino acids consisting of Arg and His, and independently thereof, variants, or fragments thereof, and independently thereof, variants, or fragments thereof, and wherein at least one proline (Pro) of said variants, or fragments thereof is substituted with an amino acid selected from the group of amino acids consisting of Phe, Tyr, Trp, and His, and independently thereof, variants, or fragments thereof, wherein at least one cysteine (Cys) of said variants, or fragments thereof is substituted with an amino acid selected from the group of amino acids consisting of Asp, Glu, Lys, Arg, His, Asn, Gln, Ser, Thr, and Tyr.

Other criteria for a variant of a peptide sequence are discussed above.

It thus follows from the above that the same functional equivalent of a peptide fragment, or fragment of said functional equivalent may comprise more than one conservative amino acid substitution from more than one group of conservative amino acids as defined herein above. The term "conservative amino acid substitution" is used synonymously herein with the term "homologous amino acid substitution". The groups of conservative amino acids are as the following:

P, A, G (neutral, weakly hydrophobic),
S, T (neutral, hydrophilic)
Q, N (hydrophilic, acid amine)
E, D (hydrophilic, acidic)
H, K, R (hydrophilic, basic)
A, L, I, V, M, F, Y, W (hydrophobic, aromatic)
C (cross-link forming)

Conservative substitutions may be introduced in any position of a preferred predetermined peptide of the invention or fragment thereof. It may however also be desirable to introduce non-conservative substitutions, particularly, but not limited to, a non-conservative substitution in any one or more positions.

A non-conservative substitution leading to the formation of a functionally equivalent fragment of the peptide of the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

According to the present invention the isolated peptide sequence as described above may be formulated as a compound, A compound may contain a single copy of an individual amino acid sequence selected from any of the described above, or it may contain two or more copies of such amino acid sequence. This means that compound of the invention may be formulated as a monomer of a peptide sequence, such as containing a single individual peptide sequence, or it may be formulated as a multimer of a peptide sequence, i.e. containing two or more individual peptide sequences, wherein said individual peptide sequences may be represented by two or more copies of the same sequence or by two or more different individual peptide sequences. The multimer may also comprise a combination of the full-length sequence and one or more fragments of said sequence. In one embodiment a compound may contain two amino acid sequences, such compound is defined herein as dimer, in another embodiment a compound may contain more then two amino acid sequences, for example three, four or more sequences. The present invention preferably relates to compounds containing two or four peptide sequences of the invention. However, compounds containing 3, 5, 6, 7, 8 or more sequences are also in the scope of the invention.

The peptide fragments formulated as dimers or multimers may have the identical amino acid sequences, or they may have different amino acid sequences. One example of such compound may be a compound containing SEQ ID NO: 1 and SEQ ID NO: 2. another example may be a compound containing SEQ ID NO: 3 and SEQ ID NO: 4. Any other combinations of the sequences of the invention may also be made. The sequences in the compound may be connected to each other via a peptide bond, or connected to each other through a linker molecule or grouping.

A compound of the invention may contain two or more identical copies of same sequence, for example two copies of a sequence selected from SEQ ID NOs: 1-26, wherein the sequences are connected other via a linker molecule or grouping. A compound wherein the sequences are connected via a linker grouping is preferred. One example of such linking grouping may be an achiral di-, tri- or tetracarboxylic acid. Suitable achiral di-, tri- or tetracarboxylic acids and a method of production such a compound (a ligand presentation assembly method (LPA) is described in WO0018791 and WO2005014623). Another example of a possible linker may be the amino acid lysine. Individual peptide sequences may be attached to a core molecule, e.g. lysine, forming thereby a dendritic multimer (dendrimer) of an individual peptide sequence(s). Production of dendrimers is also well known in the art (PCT/US90/02039, Lu et al., (1991) Mol. Immunol. 28:623-630; Defoort et al., (1992) Int J Pept Prot Res. 40:214-221; Drijfhout et al. (1991) Int J Pept Prot Res. 37:27-32), and dedrimers are at present widely used in research and in medical applications. It is a preferred embodiment of the invention to provide a dendrimeric compound comprising four individual amino acid sequences attached to the lysine core molecule. It is also preferred that at least one of the four individual amino acid sequences comprises an amino acid sequence of the formula defined above. It is even more preferred if the all four individual amino acid sequences of a dendrimeric compound individually comprise an amino acid sequence of the formula defined above.

Multimeric compounds of the invention are preferably formulated as LPA-dimers or Lysin-dendrmers. However, other types of multimeric compounds comprising two or more individual sequences of the invention may be preferred depending on the embodiments.

II Biological Activity

A peptide sequence of the invention and compound comprising a sequence of the invention possess biological activity. The invention preferably relates to biological activity selected from the capability of stimulating neural plasticity associated with neural cell differentiation, e.g. neurite outgrowth or differentiation of the neural cell precursors, stimulating neural plasticity associated with memory and learning, e.g. morphological plasticity and/or synaptic efficacy, stimulating of cell survival, e.g. inhibiting apotosis, and modulating activity of a neurotrophin receptor, e.g. a TRK receptor or p75(NTR).

Thus, in one embodiment an isolated peptide sequence as described above is capable of binding to a neurotrophin receptor, which is TRK receptor selected from TRKA, TRKB and TRKC. In one preferred embodiment, the receptor may be TRKA, in another preferred embodiment the receptor may be TRKB, in stil another preferred embodiment the receptor may be TRKC.

The authors of the present invention has identified the amino acid motifs which are present in all neurotrophins (NGF, NT-3, NT-4/5, BDNF) and associated biological activity of peptide fragments of the present invention with the presence of these motifs in their sequences. The motifs according to the invention are essential for binding of the peptide sequences of the invention to a TRK receptor, i.e. TRKA, B or C. TRK receptors are major receptors in the nervous system that drive differentiation of neural cells. TRK receptors are also important for promotion of neuronal survival and are involved in neural plasticity associated with learning and memory, i.e. TRK A, B or C.

As it was discussed above the neurotrophin receptors play an important role in normal functioning of the neural system, however, the receptors has also been associated with pathology. Thus, it has been demonstrated the potent oncogenic effects of TRKB and uncover a specific prosurvival function, the ability of TRKB to suppress anoikis (apoptosis resulting from loss of cell-matrix interactions), that may contribute to metastatic capacity of tumor cells, providing a possible explanation for the aggressive nature of human tumors that overexpress TRKB (Douma, S.; van Laar, T.; Zevenhoven, J.; Meuwissen, R.; van Garderen, E.; Peeper, D. S.: Suppression of anoikis and induction of metastasis by the neurotrophic receptor TrkB. *Nature* 430: 1034-1040, 2004); increased levels of certain neurotrophins (e.g., BDNF) have been associated with medical conditions such as epilepsy (Binder et al., Trends Neurosci. 2001, 24: 47-53).

Thus, the capability of peptide sequences of the invention of binding to the neurotrophin receptors and modulating activity of the receptors serves to modulating any biological responses dependent on the receptors activity both in normal conditions and in pathology. Accordingly, the invention provides a method of modulating activity of a neurotrophin receptor, such as of the TRK family, comprising using an isolated peptide sequence of the invention or a compound comprising said sequence. The wording "modulating activity of a neurotrophin receptor" relates to both activating and inhibiting activity of a neurotrophin receptor. In one embodiment, the invention relates to a method for activating a neurotrophin receptor, in another embodiment the invention relates to inhibiting a neurotrophin receptor. The neurotrophin receptor may in one embodiment be TRKA, in another embodiment TRKB, in still another embodiment TRKC, and yet, the receptor may in some embodiments be p75(NTR).

The isolated peptide sequence of the invention is capable of stimulating neuronal cell differentiation. The term "neuronal differentiation" is understood as both differentiation of neural precursor cells, or neural stem cells, and differentiation of neurons, such as maturation of differentiated neurons. An example of such differentiation may be neurite outgrowth from immature neurons, branching of neurites, neuron regeneration. In one preferred embodiment the invention may concern stimulating of differentiation of neural precursor/stem cells or immature neurons, in another preferred embodiment the invention may concern stimulating neurite outgrowth from mature neurons, for examples neurons which were traumatized but survived. Thus, the invention also relates to a method for stimulating of neuronal cell differentiation comprising using a peptide sequence of the invention or compound comprising said sequence.

In some preferred embodiments of the invention may concern the activity of the peptide sequences in connection with learning and memory. In particular, in one preferred embodiment the invention concerns the capability of the peptide sequences stimulate morphological plasticity of neurons, e.g. spine formation, in another preferred embodiment the invention may concern the capability of sequences to promote synaptic efficacy. Thus, the invention further relates to a method for stimulating memory and/or learning comprising using a peptide sequence of the invention and/or compound comprising said sequence. The invention relates to both short-term memory and long-term memory.

A peptide sequence of the invention is also capable of stimulating neuronal cell survival. The invention concerns the capability of stimulating neuronal cell survival both due trauma and due a degenerative disease. Accordingly, the invention further relates to a method for stimulating cell survival, preferably neuronal cell survival comprising using a peptide sequence of the invention and/or compound comprising thereof.

The peptide sequences of the invention and compounds comprising thereof are biologically active both as soluble/mobile substances of cell growth media and immobile substances of cell growth substrate. In some embodiments it may be preferred to use a peptide substance or compound comprising thereof as cell substrate. However, soluble peptide sequences or compounds comprising thereof are most preferred.

Non-limited examples of biological activity of the peptide sequences of the invention and compounds comprising thereof are described in the application (see specification of the invention below and Examples).

Stimulation of Neurite Outgrowth

Substances with the potential to promote neurite outgrowth as well as stimulate regeneration and/or differentiation of neuronal cells, such as certain endogenous trophic factors, are prime targets in the search for compounds that facilitate for example neuronal regeneration and other forms of neuronal plasticity. To evaluate the potential of the present compound, the ability to stimulate the neurite outgrowth related signalling, interfere with cell adhesion, stimulate neurite outgrowth, regeneration of nerves, may be investigated. Compounds of the present invention are shown to promote neurite outgrowth and are therefore considered to be good promoters of regeneration of neuronal connections, and thereby of functional recovery after damages as well as promoters of neuronal function in other conditions where such effect is required.

In the present context "differentiation" is related to the processes of maturation of neurons and extension of neurites, which take place after the last cell division of said neurons. The compounds of the present invention may be capable of stopping neural cell division and initiating maturation said cells, such as initiating extension of neurites. Otherwise, "differentiation" is related to initiation of the process of genetic, biochemical, morphological and physiological transformation of neuronal progenitor cells, immature neural cells or embryonic stem cells leading to formation of cells having functional characteristics of normal neuronal cell as such characteristics are defined in the art. The invention defines "immature neural cell" as a cell that has at least one feature of neural cell accepted in the art as a feature characteristic for the neural cell.

According to the present invention a compound comprising at least one of the above peptide sequences is capable of stimulating neurite outgrowth. The invention concerns the neurite outgrowth improvement/stimulation such as about 50% or 75% improvement/stimulation above the value of neurite outgrowth of control/non-stimulated cells or more strong stimulation, such as between 100%-150%, for example about 125%, such as between 150%-200%, for example about 175%, such as between 250%-300%, for example about 275%, such as between 300%-350%, for example about 325%, such as between 350%-400%, for example about 375%, such as between 400%-450%, for example about 425%, such as between 450%-500%, 500%-600% or more then 600%.

Estimation of capability of a candidate compound to stimulate neurite outgrowth may be done by using any known method or assay for estimation of neurite outgrowth, such as for example the one described in Example 1 of the present application.

According to the invention a compound has neuritogenic activity both as an insoluble immobile component of cell growth substrate and as a soluble component of cell growth media. In the present context "immobile" means that the compound is bound/attached to a substance which is insoluble in water or a water solution and thereby it becomes insoluble in such solution as well. For medical applications both insoluble and soluble compounds are considered by the application, however soluble compounds are preferred. Under "soluble compound" is understood a compound, which is soluble in water or a water solution.

Stimulation of Neuronal Survival

Substances with the potential to enhance neuronal cells to survive due to damage as well as inhibit degeneration and/or apoptosis of neuronal cells in trauma and disease, are prime targets in the search for candidate compounds for new medicine for treatment of neurodegenerative diseases such as for example Alzheimer's or Parkinson's diseases. To evaluate the potential of the present peptides, the ability to stimulate survival related signalling, interfere with apoptosis related cellular reactions, stimulate regeneration of nerves may be investigated. Compounds of the pre-sent invention are shown to promote neural cell survival and decrease the cell loss and therefore considered to be good candidates for promotion of regeneration of neural connections in brain and/or in peripheral neural system, and thereby of functional recovery after damages due trauma or disease as well as promoters of neuronal function in any other conditions where such effect is required.

In the present context "survival" is related to the processes associated with maintenance and/or recovery of cell function after the damage of the cell. The compounds of the present invention may be capable of stopping or attenuating the processes committing the cell to death, such as inhibiting apoptosis of neural cells initiated by cell damage due trauma or disease. Otherwise, "survival" is related to inhibition of the processes associated with the cell damage leading to cell death and initiation of the processes of genetic, biochemical, morphological and physiological transformation or reconstruction of cells, in particular neuronal cells, such as progenitor cells, immature neural cells or embryonic stem cells or mature neural cells having normal functional characteristics defined in the art. The invention defines "immature neural cell" as a cell that has at least one feature of neural cell accepted in the art as a feature characteristic for the neural cell.

According to the present invention a compound comprising at least one of the above peptide sequences is capable of stimulating neural cell survival. The invention concerns the neural cell survival stimulation such as about 75% stimulation above the value of survival of control/non-stimulated cells, for example 50%, such as about 150%, for example 100%, such as about 250, for example 200%, such as about 350%, for example 300%, such as about 450%, for example 400%, such as about 500%.

Estimation of capability of a candidate compound to stimulate neural cell survival may be done by using any known method or assay for estimation of cell survival, such as for example the ones described in Example 2 of the present application.

According to the invention a compound has survival promoting activity both as insoluble and soluble compound. In the present context "insoluble" means that the compound is bound/attached to a substance which is insoluble in water or a water solution and thereby the compound becomes insoluble in such solution as well. For medical applications both insoluble and soluble compounds are considered by the application, however soluble compounds are preferred. Under "soluble compound" is understood a compound, which is soluble in water or a water solution.

III Production of Individual Peptide Sequences

The peptide sequences of the present invention may be prepared by any conventional synthetic methods, recombinant DNA technologies, enzymatic cleavage of full-length proteins which the peptide sequences are derived from, or a combination of said methods.

Recombinant Preparation

Thus, in one embodiment the peptides of the invention are produced by use of recombinant DNA technologies.

The DNA sequence encoding a peptide or the corresponding full-length protein the peptide originates from may be prepared synthetically by established standard methods, e.g. the phosphoamidine method described by Beaucage and Caruthers, 1981, Tetrahedron Lett. 22:1859-1869, or the method described by Matthes et al., 1984, EMBO J. 3:801-805. According to the phosphoamidine method, oligonucleotides are synthesised, e.g. in an automatic DNA synthesiser, purified, annealed, ligated and cloned in suitable vectors.

The DNA sequence encoding a peptide may also be prepared by fragmentation of the DNA sequences encoding the corresponding full-length protein of peptide origin, using DNAase I according to a standard protocol (Sambrook et al., Molecular cloning: A Laboratory manual. 2rd ed., CSHL Press, Cold Spring Harbor, N.Y., 1989). The present invention relates to full-length proteins selected from the groups of proteins identified above. The DNA encoding the full-length proteins of the invention may alternatively be fragmented using specific restriction endonucleases. The fragments of DNA are further purified using standard procedures described in Sambrook et al., Molecular cloning: A Laboratory manual. 2rd ed., CSHL Press, Cold Spring Harbor, N.Y., 1989.

The DNA sequence encoding a full-length protein may also be of genomic or cDNA origin, for instance obtained by preparing a genomic or cDNA library and screening for DNA sequences coding for all or part of the full-length protein by hybridisation using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al., 1988, Science 239:487-491.

The DNA sequence is then inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding a peptide or a full-length protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the SV 40 promoter (Subramani et al., 1981, Mol. Cell. Biol. 1:854-864), the MT-1 (metallothionein gene) promoter (Palmiter et al., 1983, Science 222: 809-814) or the adenovirus 2 major late promoter. A suitable promoter for use in insect cells is the polyhedrin promoter (Vasuvedan et al., 1992, FEBS Lett. 311:7-11). Suitable promoters for use in yeast host cells include promoters from yeast glycolytic genes (Hitzeman et al., 1980, J. Biol. Chem. 255:12073-12080; Alber and Kawasaki, 1982, J. Mol. Appl. Gen. 1: 419-434) or alcohol dehydrogenase genes (Young et al., 1982, in Genetic Engineering of Microorganisms for Chemicals, Hollaender et al, eds., Plenum Press, New York), or the TPI1 (U.S. Pat. No. 4,599,311) or ADH2-4-c (Russell et al., 1983, Nature 304: 652-654) promoters. Suitable promoters for use in filamentous fungus host cells are, for instance, the ADH3 promoter (McKnight et al., 1985, EMBO J. 4:2093-2099) or the tpiA promoter.

The coding DNA sequence may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the peptides or full-length proteins, the promoter and the terminator, respectively, and to insert them into suitable vectors containing the information necessary for replication, are well known to persons skilled in the art (cf., for instance, Sambrook et al., op. cit.).

To obtain recombinant peptides of the invention the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-S-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK, thrombin, with the amino acid sequence LVPR/GS, or *Acharombacter lyticus*, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines are the HEK293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are described in e.g. Kaufman and Sharp, J. Mol. Biol. 159, 1982, pp. 601-621; Southern and Berg, 1982, J. Mol. Appl. Genet, 1:327-341; Loyter et al., 1982, Proc. Natl. Acad. Sci. USA 79: 422-426; Wigler et al., 1978, Cell 14:725; Corsaro and Pearson, 1981, in Somatic Cell Genetics 7, p. 603; Graham and van der Eb, 1973, Virol. 52:456; and Neumann et al., 1982, EMBO J. 1:841-845.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be pre-pared according to published recipes (e.g. in catalogues of the American Type Culture Collection).

The peptides or full-length proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

Synthetic Preparation

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

Peptides may for example be synthesised by using Fmoc chemistry and with Acm-protected cysteins. After purification by reversed phase HPLC, peptides may be further processed to obtain for example cyclic or C- or N-terminal modified isoforms. The methods for cyclization and terminal modification are well-known in the art and described in detail in the above-cited manuals.

In a preferred embodiment the peptide sequences of the invention are produced synthetically, in particular, by the Sequence Assisted Peptide Synthesis (SAPS) method.

By SAPS peptides may be synthesised either batchwise in a polyethylene vessel equipped with a polypropylene filter for filtration or in the continuous-flow version of the polyamide solid-phase method (Dryland, A. and Sheppard, R. C., (1986) J. Chem. Soc. Perkin Trans. I, 125-137) on a fully automated peptide synthesiser using 9-fluorenylmethyloxycarbonyl (Fmoc) or tert.-Butyloxycarbonyl, (Boc) as N-a-amino protecting group and suitable common protection groups for side-chain functionality.

When synthesised, individual peptide sequences may then be formulated as multimers using well-known in the art techniques, for examples dimers of the sequences may be obtained by the LPA method described in WO 00/18791, denrimeric polymers by the MAP synthesis described in PCT/US90/02039.

IV Antibody

It is an objective of the present invention to provide an antibody, antigen binding fragment or recombinant protein thereof capable of recognizing and selectively binding to an epitope on NGF, NT-3, NT-4/5, BDNF, said epitope comprising a motif of the invention or a sequence selected from SEQ ID NOs:1-26, or a fragment of said sequence.

By the term "epitope" is meant the specific group of atoms (on an antigen molecule) that is recognized by (that antigen's) antibodies (thereby causing an immune response). The term "epitope" is the equivalent to the term "antigenic determinant". The epitope may comprise 3 or more amino acid residues, such as for example 4, 5, 6, 7, 8 amino acid residues, located in close proximity, such as within a contiguous amino acid sequence, or located in distant parts of the amino acid sequence of an antigen, but due to protein folding have been approached to each other.

Antibody molecules belong to a family of plasma proteins called immunoglobulins, in whose basic building block, the immunoglobulin fold or domain, is used in various forms in many molecules of the immune system and other biological recognition systems. A typical immunoglobulin has four polypeptide chains, containing an anti-gen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Novotny J, & Haber E. Proc Natl Acad Sci USA. 82(14):4592-6, 1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and react with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

The term "antibody fragment" is used herein interchangeably with the term "antigen binding fragment".

Antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it is has similar or immunological properties relative to antibody that binds with specificity to an epitope comprising a peptide sequence selected from any of the sequences identified herein as SEQ ID NOs: 1-22, or a fragment of said sequences. Thus, in context of the present invention the term "antibody fragment" is identical to term "antigen binding fragment".

Antibody fragments retain some ability to selectively bind with its antigen or receptor. Some types of antibody fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per anti-body molecule.

Fab' fragments differ from Fab fragments by the addition of a few residues at the carboxyl terminus of the heavy chain CH1 domain including one or more cysteines from the antibody hinge region.

(3) (Fab')₂ is the fragment of an antibody that can be obtained by treating whole antibody with the enzyme pepsin without subsequent reduction.

(4) F(ab')₂ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies 113: 269-315 Rosenburg and Moore eds. Springer-Verlag, NY, 1994.

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad. Sci. USA 90: 6444-6448 (1993).

The invention contemplate both polyclonal and monoclonal antibody, antigen binding fragments and recombinant proteins thereof which are capable of binding an epiyope according to the invention.

The preparation of polyclonal antibodies is well-known to those skilled in the art. See, for example, Green et al. 1992. Production of Polyclonal Antisera, in: Immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1, which are hereby incorporated by reference.

The preparation of monoclonal antibodies likewise is conventional. See, for example, Kohler & Milstein, Nature, 256: 495-7 (1975); Coligan, et al., sections 2.5.1-2.6.7; and Harlow, et al., in: Antibodies: A Laboratory Manual, page 726, Cold Spring Harbor Pub. (1988), Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG). In: Methods in Molecular Biology, 1992, 10:79-104, Humana Press, NY.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, 1975, Nature 256, 495-7, or may be made by recombinant methods, e.g., as described in U.S. Pat. No. 4,816,567. The monoclonal antibodies for use with the present invention may also be isolated from phage antibody libraries using the techniques described in Clackson et al., 1991, Nature 352: 624-628, as well as in Marks et al., 1991, J Mol Biol 222: 581-597. Another method involves humanizing a monoclonal antibody by recombinant means to generate antibodies containing human specific and recognizable sequences. See, for review, Holmes, et al., 1997, J Immunol 158:2192-2201 and Vaswani, et al., 1998, Annals Allergy, Asthma & Immunol 81:105-115.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in anti-bodies derived from another species or belonging to another antibody class or subclass, as well as fragments of such antibodies, so long as they exhibit the desired biological activity (U.S. Pat. No. 4,816,567); Morrison et al., 1984, Proc Natl Acad Sci 81: 6851-6855.

Methods of making antibody fragments are also known in the art (see for example, Harlow and Lane, Antibodies: A Laboratory Manual, Cold Spring Harbor Laboratory, NY, 1988, incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted F(ab')₂. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. No. 4,036,945 and U.S. Pat. No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain anti-gen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow, et al., 1991, In: Methods: A Companion to Methods in Enzymology, 2:97; Bird et al., 1988, Science 242:423-426; U.S. Pat. No. 4,946,778; and Pack, et al., 1993, BioTechnology 11:1271-77.

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', F(ab')$_2$ or other antigen-binding subsequences of antibodies) that contain a minimal sequence derived from non-human immunoglobulin, such as the eitope recognising sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Humanized antibody(es) containing a minimal sequence(s) of antibody(es) of the invention, such as a sequence(s) recognising the epitope(s) described herein, is one of the preferred embodiments of the invention.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., 1986, Nature 321, 522-525; Reichmann et al., 1988, Nature 332, 323-329; Presta, 1992, Curr Op Struct Biol 2:593-596; Holmes et al., 1997, J Immunol 158:2192-2201 and Vaswani, et al., 1998, Annals Allergy, Asthma & Immunol 81:105-115.

The generation of antibodies may be achieved by any standard method in the art for producing polyclonal and monoclonal antibodies using natural or recombinant fragments of human NGF, NT-3, NT-4/5, BDNF, said fragment comprising a sequence selected from SEQ ID NO: 1-26, as an antigen. Such antibodies may be also generated using variants, homologues or fragments of peptide sequences of SEQ ID NOs:1-26, said variants, homologues and fragments are immunogenic peptide sequences which meet the following criteria:
(i) being a contiguous amino acid sequence of at least 5 amino acids;
(ii) comprising a motif of the invention.

The antibodies may also be produced in vivo by the individual to be treated, for example, by administering an immunogenic fragment according to the invention to said individual. Accordingly, the present invention further relates to a vaccine comprising an immunogenic fragment described above.

The application also relates to a method for producing an antibody of the invention said method comprising a step of providing of an immunogenic fragment described above.

The invention relates both to antibodies, which are capable of modulating, such as enhancing or attenuating, biological function of NGF, NT-3, NT-4/5, BDNF, in particular a function related to neural cell differentiation, survival and/or plasticity, and to an antibody, which can recognise and specifically bind the latter proteins without modulating biological activity thereof.

The invention relates to use of the above antibodies for 1) therapeutic applications when the modulation of activity of human NGF, NT-3, NT-4/5, BDNF, is beneficial for treatment, 2) detecting and/or monitoring the latter proteins in vitro and/or in vivo for diagnostic purposes, 3) research purposes.

V Pharmaceutical Composition

The invention also relates to a pharmaceutical composition comprising one or more of the compounds defined above, wherein the compound is capable of stimulating neurite outgrowth and/or neural cell differentiation, survival of neural cells and/or stimulating learning and/or memory. Thus, the invention concerns a pharmaceutical composition capable of stimulating differentiation of neuronal cells and/or stimulating regeneration of neuronal cells, and/or stimulating neuronal plasticity in connection with learning and memory, and/or stimulating survival of neural cells.

In the present context the term "pharmaceutical composition" is used synonymously with the term "medicament".

In a composition the peptide sequences may be formulated as comprising isolated individual peptide fragments or multimers or dimers thereof as discussed above.

The pharmaceutical composition may have the described above effects on cells in vitro or in vivo, wherein the composition is administered to a subject.

The medicament of the invention comprises an effective amount of one or more of the compounds as defined above, or a composition as defined above in combination with the pharmaceutically acceptable additives. Such medicament may suitably be formulated for oral, percutaneous, intramuscular, intravenous, intracranial, intrathecal, intracerebroventricular, intranasal or pulmonal administration.

Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules, nanoparticles or the like.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

Other formulations are such suitable for nasal and pulmonal administration, e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred µg active ingredient per administration with a preferred range of from about 0.1 µg to 5000 µg per kilo body weight. Using monomeric forms of the compounds, the suitable dosages are often in the range of from 0.1 µg to 5000 µg per kilo body weight, such as in the range of from about 0.1 µg to 3000 µg per kilo body weight, and especially in the range of from about 0.1 µg to 1000 µg per kilo body weight. Using multimeric forms of the compounds, the suitable dosages are often in the range of from 0.1 µg to 1000 µg per kilo body weight, such as in the range of from about 0.1 µg to 750 µg per kilo body weight, and especially in the range of from about 0.1 µg to 500 µg per kilo body weight such as in the range of from about 0.1 µg to 250 µg per kilo body weight. In particular when administering nasally smaller dosages are used than when administering by other routes. Administration may be performed once or may be followed by subsequent administrations. The dosage will also depend on the route of administration and will vary with the age and weight of the subject to be treated. A preferred dosage of multimeric forms would be in the interval 1 mg to 70 mg per 70 kg body weight.

For some indications a localised or substantially localised application is preferred.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promotes delivery of the active substance to its target.

In many instances, it will be necessary to administer the formulation multiple times. Administration may be a continuous infusion, such as intraventricular infusion or administration in more doses such as more times a day, daily, more times a week, weekly, etc. It is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long term effect whereby administration of the compounds may be conducted with long intervals, such as 1 week or 2 weeks.

In connection with the use in nerve guides, the administration may be continuous or in small portions based upon controlled release of the active compound(s). Furthermore, precursors may be used to control the rate of release and/or site of release. Other kinds of implants and well as oral administration may similarly be based upon controlled release and/or the use of precursors.

As discussed above, the present invention relates to treatment of individuals for inducing differentiation, stimulating regeneration, plasticity and survival of neural cells in vitro or in vivo, said treatment involving administering an effective amount of one or more compounds as defined above.

Another strategy for administration is to implant or inject cells capable of expressing and secreting the compound in question. Thereby the compound may be produced at the location where it is going to act.

VI Treatment

In a further aspect, the present invention relates to said peptides, fragments, or variants thereof for use in the induction of differentiation and/or stimulation of regeneration, plasticity and/or survival of neural cells. The use is for the treatment for pre-venting diseases and conditions of the central and peripheral nervous system, and of the muscles or of various organs.

Treatment by the use of the compounds/compositions according to the invention is in one embodiment useful for inducing differentiation, modulating proliferation, stimulate regeneration, neuronal plasticity and survival of cells being implanted or transplanted. This is particularly useful when using compounds having a long term effect.

Thus, the treatment comprises treatment and/or prophylaxis of cell death in relation to diseases or conditions of the central and peripheral nervous system, such as postoperative nerve damage, traumatic nerve damage, e.g. resulting from spinal cord injury, impaired myelination of nerve fibers, postischaemic damage, e.g. resulting from a stroke, multiinfarct dementia, multiple sclerosis, nerve degeneration associated with diabetes mellitus, neuro-muscular degeneration, schizophrenia, Alzheimer's disease, Parkinson's disease, or Huntington's disease.

Also, in relation to diseases or conditions of the muscles including conditions with impaired function of neuro-muscular connections, such as genetic or traumatic atrophic muscle disorders; or for the treatment of diseases or conditions of various organs, such as degenerative conditions of the gonads, of the pancreas, such as diabetes mellitus type I and II, of the kidney, such as nephrosis the compounds according to the invention may be used for inducing differentiation, modulating proliferation, stimulate regeneration, neuronal plasticity and survival, i.e. stimulating survival.

In yet a further embodiment the use of the compound and/or pharmaceutical composition is for the stimulation of the ability to learn and/or of the short and/or long term memory.

In particular the compound and/or pharmaceutical composition of the invention may be used in the treatment of clinical conditions, such as psychoses, such as senile and presenile organic psychotic conditions, alcoholic psychoses, drug psychoses, transient organic psychotic conditions, Alzheimer's disease, cerebral lipidoses, epilepsy, general paresis [syphilis], hepatolenticular degeneration, Huntington's chorea, Jakob-Creutzfeldt disease, multiple sclerosis, Pick's disease of the brain, syphilis, Schizophrenic disorders, affective psychoses, neurotic disorders, personality disorders, including character neurosis, nonpsychotic personality disorder associated with organic brain syndromes, paranoid personality disorder, fanatic personality, paranoid personality (disorder), paranoid traits, sexual deviations and disorders, mental retardation, disease in the nervesystem and sense organs, cognitive anomalies, inflammatory disease of the central nervous system, such as meningitis, encephalitis; cerebral degenerations such as Alzheimer's disease, Pick's disease, senile degeneration of brain, communicating hydrocephalus, obstructive hydrocephalus, Parkinson's disease including other extra pyramidal disease and abnormal movement disorders, spinocerebellar disease, cerebellar ataxia, Marie's, SangerBrown, Dyssynergia cerebellaris myoclonica, primary cerebellar degeneration, such as spinal muscular atrophy, familial, juvenile, adult spinal muscular atrophy, motor neuron disease, amyotrophic lateral sclerosis, motor neuron disease, progressive bulbar palsy, pseudobulbar palsy, primary lateral sclerosis, other anterior horn cell diseases, anterior horn cell disease, unspecified, other diseases of spinal cord, syringomyelia and syringobulbia, vascular myelopathies, acute infarction of spinal cord (embolic) (nonembolic), arterial thrombosis of spinal cord, edema of spinal cord, subacute necrotic myelopathy, subacute combined degeneration of spinal cord in diseases classified elsewhere, myelopathy, drug-induced, radiation-induced myelitis, disorders of the autonomic nervous system, disorders of peripheral autonomic, sympathetic, parasympathetic, or vegetative system, familial dysautonomia [RileyDay syndrome], idiopathic peripheral autonomic neuropathy, carotid sinus syncope or syndrome, cervical sympathetic dystrophy or paralysis; peripheral autonomic neuropathy in disorders classified elsewhere, amyloidosis, diseases of the peripheral nerve system, brachial plexus lesions, cervical rib syndrome, costoclavicular syndrome, scalenus anterior syndrome, thoracic outlet syndrome, brachial neuritis or radiculitis, including in newborn. Inflammatory and toxic neuropathy, including acute infective polyneuritis, Guillain-Barre syndrome, Postinfectious polyneuritis, polyneuropathy in collagen vascular disease, disorders affecting multiple structures of eye, purulent endophthalmitis, diseases of the ear and mastoid process, abnormality of organs and soft tissues in newborn, including in the nerve system, complications of the administration of anesthetic or other sedation in labor and delivery, diseases in the skin including infection, insufficient circulation problem, injuries, including after surgery, crushing injury, burns. Injuries to nerves and spinal cord, including division of nerve, lesion in continuity (with or without open wound), traumatic neuroma (with or without open wound), traumatic transient paralysis (with or without open wound), accidental puncture or laceration during medical procedure, injury to optic nerve and pathways, optic nerve injury, second cranial nerve, injury to optic chiasm, injury to optic pathways, injury to visual cortex, unspecified blindness, injury to other cranial nerve(s), injury to other and unspecified nerves. Poisoning by drugs, medicinal and biological substances, genetic or traumatic atrophic muscle disorders; or for the treatment of diseases or conditions of various organs, such as degenerative conditions of the gonads, of the pancreas, such as diabetes mellitus type I and II, of the kidney, such as nephrosis.

A further aspect of the invention is a process of producing a pharmaceutical composition, comprising mixing an effective amount of one or more of the compounds of the invention, or a pharmaceutical composition according to the invention with one or more pharmaceutically acceptable additives or carriers, and administer an effective amount of at least one of said compound, or said pharmaceutical composition to a subject.

In one embodiment of the process as mentioned above, the compounds are used in combination with a prosthetic device, wherein the device is a prosthetic nerve guide. Thus, in a further aspect, the present invention relates to a prosthetic nerve guide, characterised in that it comprises one or more of the compounds or the pharmaceutical composition as defined above. Nerve guides are known in the art.

Another aspect of the invention relates to the use of a compound as defined above. In particular the use of a compound according to the invention is for the production of a pharmaceutical composition. The pharmaceutical composition is preferably for the treatment or prophylaxis of any of the diseases and conditions mentioned above.

In yet a further aspect the invention relates to a method of treating a disease or condition as discussed above by administering a compound as defined herein.

EXAMPLES

Methods

Neurite Outgrowth of Primary Neurons in Culture

Dissociated cerebellar neurons were isolated from 7 day old rats. Cerebellum was isolated from the brain in ice cold modified Krebs Ringer solution, cleared of blood vessels, roughly homogenised by chopping and then trypsinised. The dissociated cells were washed in the presence of DNAse 1 and soybean trypsin inhibitor. Postnatal hippocampal neurons or cerebellar granule neurons (CGN) were plated at a density of 10,000 cells/cm$^2$ on uncoated 8-well permanox Lab-Tek chamber slides in Neurobasal medium supplemented with 0.4% (w/v) bovine serum albumin (BSA; Sigma-Aldrich), 2% (v/v) B27 Neurobasal supplement, 1% (v/v) glutamax, 100 U/ml penicillin, 100 µg/ml streptomycin and 2% 1 M HEPES (all from Gibco, BRL). After 24 hours, the neurons were fixed with 4% (v/v) formaldehyde for 20 minutes and thereafter immunostained using primary rabbit antibodies against GAP-43 and Alexa Fluor secondary goat anti-rabbit Ig antibodies. Images of at least 200 neurons for each group in each individual experiment were obtained systematically by computer assisted fluorescence microscopy as previously described (Rønn et al., 2000). Briefly, a Nikon Diaphot inverted microscope with a Nikon Plan 20× objective (Nikon, Tokyo, Japan) coupled to a video camera (Grundig Electronics, Germany) was used for recordings. A software package Prima developed at the Protein Laboratory (Copenhagen, Denmark) was used to make a stereologically based determination of neurite length (Rønn et al., 2000).

Neuronal Cell Survival in Primary Culture

Primary cultures of CGN were plated at a density of 10 cells/cm² on poly-Llysine coated 8-well permanox slides in Neurobasal—A medium (Gibco BRL) supplemented with 2% (v/v) B27, 0.5% (v/v) glutamax, 100 units/mL penicillin, 100 μg/mL streptomycin and KCl, making the final concentration of KCl in the medium 40 mm. Twenty-four hours after plating, cytosine-D-arabinofuranoside (Ara-C; Sigma-Aldrich) was added to a final concentration of 10 μm to avoid proliferation of glial cells, after which the neurons were allowed to differentiate for a further 6 days at 37° C. Apoptotic cell death was induced by washing twice and changing the medium to Basal Medium Eagle (BME; Gibco BRL) supplemented with 1% (v/v) glutamine, 100 U/mL penicillin and 100 μg/mL streptomycin, 3.5 g d-glucose/L and 1% (v/v) sodium pyruvate (Gibco BRL) together with various concentrations of peptide. Thereby the concentration of potassium in the cultures was reduced to 5 mm KCl. Two days after induction of apoptosis, the cells were fixed with 4% (v/v) formaldehyde and stained with Hoechst 33258 (D'Merllo et al., 1993).

Traumatic Brain Injury Model

A focal brain injury on the right fronto-parietal cortex was made by applying a piece of dry-ice (−78° C.) directly onto the skull for 30 seconds in mice and 60 seconds in rats, as previously described in details (Penkowa et al., 2003).

Tissue Processing

Histochemistry and immunohistochemistry were performed on sections cut from organs taken from fixated animals. Rats and mice were deeply anesthetized with Brietal and flushed by cardiac perfusion with saline containing heparine (0.9% NaCl, 3 ml/L 5000 IU heparine) for 2 minutes followed by fixation with Zamboni's fixative (pH 7.4) for 4-8 minutes depending on the size of the animal. For immunohistochemical investigation, brain were dissected and postfixed in Zamboni's for 2-3 hours, dehydraded in graded alcohol followed by xylol and subsequently embedded in paraffin before being cut in 3 μm frontal sections throughout the entire area of the cryo lesion. For heat-induced epitope retrieval, the sections were boiled in citrate buffer (pH 6 or 9) in a microwave oven for 10 minutes followed by incubation in 10% goat serum (In Vitro, Fredensborg, DK) or donkey serum (code BP 005.1; The Binding Site, Birmingham, UK) in tris buffered saline (TBS)/Nonidet P-40 (0.01%) for 30 minutes at room temperature. Sections with mouse tissue used for incubation with monoclonal mouse-derived antibodies were also incubated with Blocking Solutions A+B from the HistoMouse-SP kit to quench endogenous mouse IgG (Zymed, Calif., USA).

Immunohistochemistry and Histochemistry

Following treatment as described above, sections were incubated overnight at 5° C. with one of the following primary antibodies: polyclonal rabbit anti-cow glial fibrillary acidic protein (GFAP) 1:250 (a marker for astrocytes; DakoCytomation); monoclonal mouse anti-8-hydroxydeoxyguanosine (8-OH-dG) diluted 1:100 in goat serum (a marker for DNA oxidation; Chemicon, Temacula, Calif., USA). The primary antibody was detected with biotynilated secondary antibodies, incubated with streptavidin-biotin-peroxidase complex for 30 min. Biotinylated tomato lectin (Sigma, Vallensbæk, DK) was used as a marker for microglia/macrophages. The lectin staining was further developed by using a streptavidin-biotin-peroxidase complex (StreptABComplex/HRP; DakoCytomation, Glostrup, DK) as described by the manufacturer and performed for 30 minutes at room temperature (RT). The lectin reaction product was visualized by using 0.015% $H_2O_2$ in 3,3'-diaminobenzidine/TBS (DAB/TBS) with DAB as chromogen.

```
NGF-derived peptides:
NGF-C2     CVLSRKAVRRA              SEQ ID NO: 7

NGF-D      amino acids 2-14 of SEQ ID NO: 1

NGF-E      RGIDSKHWNSY              SEQ ID NO: 19

NGF-C1     RIDTACV                  SEQ ID NO: 5

NGF-EE,    TFVKALTMDGKQAAWR         SEQ ID NO: 15

NGF-N      SSHPIFHRGEFS             SEQ ID NO: 11

BDN F-derived peptides
BDNF-E     RGIDKRHWNSQ              SEQ ID NO: 22

BDNF-EE    SYVRALTMDSKKRIGWR        SEQ ID NO: 18
```

Results

Example 1

Stimulation of Neurite Outgrowth

CGN prepared as described above were treated with different concentrations (3-81 μg/ml) of peptides NGF-C2, NGF-D, NGF-E, NGF-C1, NGF-EE, BDNF-E or BDNF-EE.

From FIGS. 1, 2, 4 and 5 it could be seen that peptides NGF-C2 (motif II), NGF-E (motif III), NGF-C1 (motif I), NGF-EE (motif III), BDNF-E (motif III) or BDNF-EE (motif III) comprising the indicated structural motifs all significantly stimulate neurite outgrowth form primary neurons in culture. In contrast peptide NGF-D, which lacks the essential hydrophobic residue of motif I, does not have neuritogenic activity (FIG. 1).

Example 2

Stimulation of Neuronal Cell Survival

Examination of the effect of different peptides on survival of neurons was performed both in vivo and in vitro For in vitro experiments cultures of CGR neurons were prepared as above and treated with different concentrations of NGF-E, NGF-EE or NGF-N.

Figure 3:
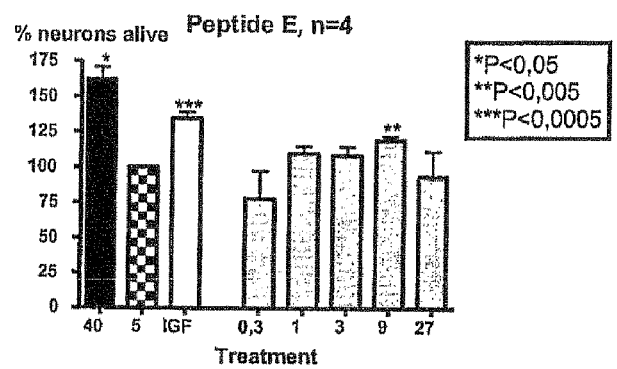
FIG. 3 demonstrates the effect of NGF-derived peptides, NGF-E, NGF-EE and NGF-N, on survival of CGN FIG. 4 demonstrates the effect of a BDNF-derived peptide, BDNF-E, on neurite outgrowth from CGN FIG. 5 demonstrates the effect of a BDNF-derived peptide, BDNF-EE; on neurite outgrowth from CGN
Figure 3:
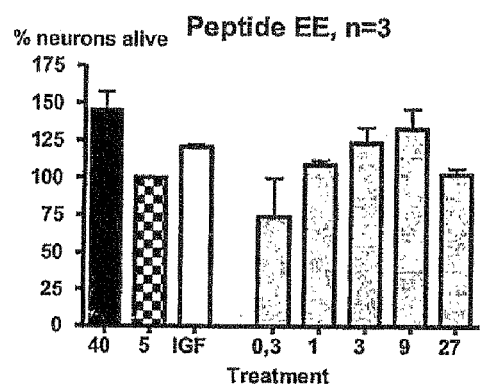
Figure 3:
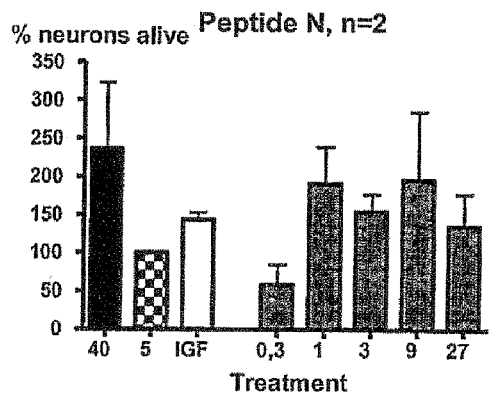
Figure 4:
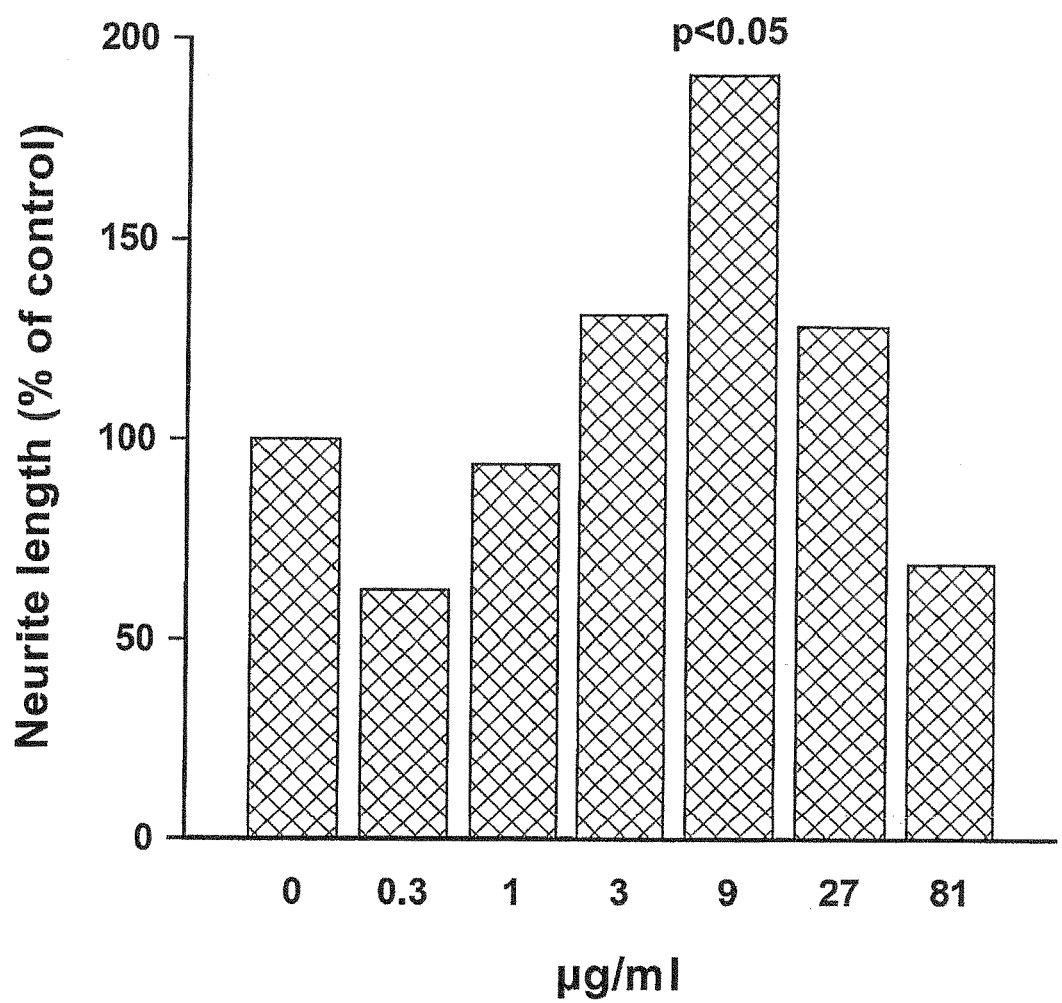
Figure 5:
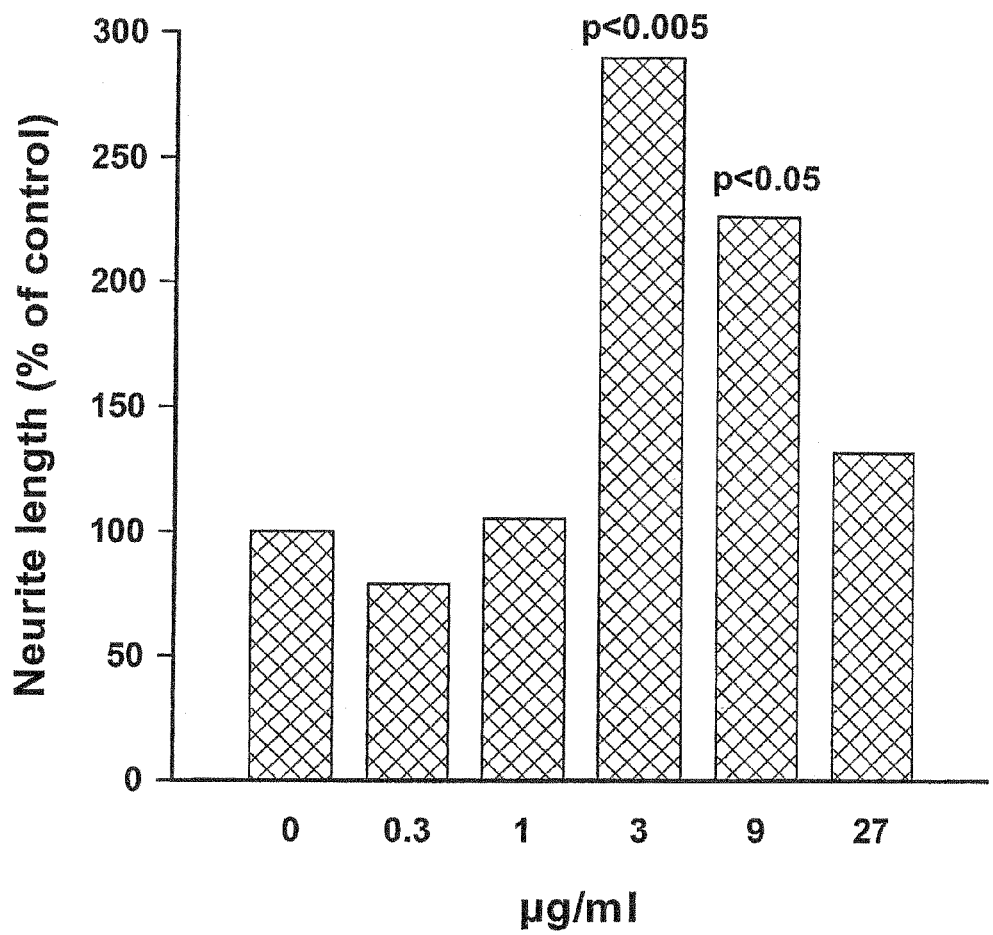

From FIG. 3 it can be seen that all tested peptides significantly promote survival of CGN in culture In vivo experiments—A focal brain injury on the right fronto-parietal cortex was made by applying a piece of dry-ice (−78° C.) directly onto the skull for 30 seconds in mice and 60 seconds in rats, as previously described in details (Penkowa et al., 2003). A focal brain injury on the right fronto-parietal cortex was made by applying a piece of dry-ice (−78° C.) directly onto the skull for 30 seconds in mice and 60 seconds in rats, as previously described in details (Penkowa et al., 2003). Following treatment, as described below, sections were incubated overnight at 5° C. with one of the following primary antibodies: polyclonal rabbit anti-cow glial fibrillary acidic protein (GFAP) 1:250 (a marker for astrocytes; Dako-Cytomation); monoclonal mouse anti-8-hydroxydeoxyguanosine (8-OH-dG) diluted 1:100 in goat serum (a marker for DNA oxidation; Chemicon, Temacula, Calif., USA). The primary antibody was detected with biotynilated secondary antibodies, incubated with streptavidin-biotin-peroxidase complex for 30 min. Biotinylated tomato lectin (Sigma, Vallensbæk, DK) was used as a marker for microglia/macrophages. The lectin staining was further developed by using a streptavidin-biotin-peroxidase complex (StreptABComplex/HRP; DakoCytomation, Glostrup, DK) as described by the manufacturer and performed for 30 minutes at room temperature (RT). The lectin reaction product was visualized by using 0.015% $H_2O_2$ in 3,3'-diaminobenzidine/TBS (DAB/TBS) with DAB as chromogen. Animals were treated on day (−1), 1 and 3 following the lesion with a peptide (10 mg/kg/injection) injected subcutaneously.

Treatment of lesioned rats with the BDNF-EE peptide results in inhibition of oxidative stress as reflected by immunostaining for 8-hydroxydeoxyguanosine, a marker for DNA oxidation, inhibition of microglia activation as reflected by binding of tomato lectin, a marker of activated microglia and in an activation of cortical astrocytes as reflected by immunostaining for GFAP.

Example 3

Binding of NGF and BDNF Derived Peptides to TrkA, TrkB, TrkC and P75

Surface Plasmone Resonance (SPR) Analysis

Analysis of binding of NGF derived peptides NGF-C2, NGF-E, NGF-EE and NGF and BDNF derived peptides BDNF-C1, BDNF-C2, BDNF-E, BDNF-EE, and BDNF to the Trk-receptors TrkA, TrkB, TrkC, and the P75 receptor was performed by Surface Plasmon Resonance (SPR) using a BIAlite instrument (Biacore AB, Uppsala, Sweden) at 25° C. using HBS-EP running buffer, containing 10 mM Hepes, pH 7.4, 150 mM NaCl, 3 mM EDTA and 0.005% P20. The TrkA, TrkB and TrkC receptors and p75$^{NTR}$ were immobilized on a sensor chip, CM4, using an amine-coupling kit as follows: the chip was activated by 20 μl activation solution, N-hydroxysuccinimide, (NHS) and N-ethyl-N'-(3-diethylaminopropyl)-carbodiimide (EDC), the protein was immobilized using 30 μl of a mixture of 4 μl (0.5 μg/ml) protein in 50 μl 10 mM sodium acetate buffer (pH 4.0); and the chip was blocked by 35 μl blocking solution (ethanolamine-HCl). The receptor surface was regenerated between ligand injections with 15 μl 2 mM NaCl or 10 mM glycine-HCl, pH 2.5. In the present experiments a flow rate of 5 μl/min was used.

The curve corresponding to the difference between binding to the Trk receptors or the p755$^{NTR}$ receptor and a blank chip was used for analysis.

Calculated affinity constants (KD) are displayed in table 1.

TABLE 1

| Ligand | TrkA/KD (M) | TrkB/KD (M) | TrkC/KD (M) | P75/KD (M) |
|---|---|---|---|---|
| NGF-C2 | $7.27 \times 10^{-7}$ | $8.83 \times 10^{-7}$ | $6.58 \times 10^{-7}$ | $3.85 \times 10^{-7}$ |
| NGF-E | (−) | $2.54 \times 10^{-7}$ | $1.06 \times 10^{-6}$ | $2.60 \times 10^{-6}$ |
| NGF-EE | (−) | $1.03 \times 10^{-8}$ | $5.19 \times 10^{-8}$ | $2.26 \times 10^{-7}$ |
| NGF | $4.63 \times 10^{-9}$ | $9.94 \times 10^{-9}$ | $3.56 \times 10^{-8}$ | $1.65 \times 10^{-8}$ |
| BDNF-C1 | (−) | $1.04 \times 10^{-6}$ | $3.50 \times 10^{-6}$ | $1.20 \times 10^{-6}$ |
| BDNF-C2 | (−) | $4.08 \times 10^{-8}$ | $1.11 \times 10^{-7}$ | $3.31 \times 10^{-7}$ |
| BDNF-E | (−) | $1.73 \times 10^{-7}$ | $6.97 \times 10^{-7}$ | $5.56 \times 10^{-7}$ |
| BDNF-EE | (−) | $3.87 \times 10^{-8}$ | $1.66 \times 10^{-7}$ | $1.10 \times 10^{-7}$ |
| BDNF | (−) | $1.18 \times 10^{-9}$ | $1.40 \times 10^{-8}$ | $5.84 \times 10^{-11}$ |

The invention claimed is:

1. A method of stimulating neurite outgrowth or neuronal cell survival which comprises contacting a neuronal cell with an effective amount of (1) a peptide sequence consisting of 10 to 25 contiguous amino acid residues, comprising at least the amino acid motif of the formula $$x^{p1}\text{-D/E-T-}x^{a1}\text{-C (motif I), wherein}$$

$x^{p1}$ is Y or I, and
$x^{a1}$ is K, R, S, or A, or (2) a compound which is a multimer consisting of two or more individual peptide sequences, which may be the same or different, according to (1), and optionally at least one linker covalently connecting at least two such individual peptide sequences.

2. The method according to claim 1, wherein said peptide sequence is capable of stimulating neurite outgrowth.

3. The method according to claim 1, wherein said peptide sequence is capable of stimulating neural plasticity, such neural plasticity associated with learning and/or memory.

4. The method according to claim 1, wherein said peptide is capable of stimulating neuronal cell differentiation.

5. The method according to claim 1, wherein said peptide sequence is capable of modulating activity of a neurotrophin receptor.

6. The method according to claim 5, wherein said sequence is capable of activating a neurotrophin receptor.

7. The method according to claim 5, wherein said sequence is capable of inhibiting a neurotrophin receptor.

8. The method according to claim 5, wherein the neurotrophin receptor is Trk A, Trk B or Trk C.

9. The method according to claim 5, wherein the neurotrophin receptor is p75$^{Trk}$.

10. The method according to claim 5, wherein said peptide sequence is capable of stimulating cell survival.

11. The method according to claim 1, wherein said peptide sequence is derived from nerve growth factor (NGF).

12. The method according to claim 11, wherein the sequence is SEQ ID NO: 1, 5 or 23.

13. The method according to claim 1, wherein said sequence is derived from neurotrophin-3 (NT-3).

14. The method according to claim 13, wherein the sequence is SEQ ID NO: 24 or 6.

15. The method according to claim 1, wherein said sequence is derived from neurotrophin-4/5 (NT-4/5).

16. The method according to claim 15, wherein the sequence is SEQ ID NO: 3, 25 or 5.

17. The method according to claim 1, wherein said sequence is derived from brain-derived neurotrophic factor (BDNF).

18. The method according to claim 17, wherein the sequence is SEQ ID NO: 26 or 6.

19. The method of claim 1, wherein the multimer is a dendrimer.

20. The method according to claim 1, wherein said sequence is selected from the following amino acid sequences
YETKCRDPNPVDSG (SEQ ID NO: 1),
YETRCKADNAEEGGPGAG (SEQ ID NO: 3),
RIDTACV (SEQ ID NO:5),
RIDTSCV (SEQ ID NO:6),
RIDTACVCVLSRKAVRRA (SEQ ID NO:23),
RIDTSCVCALSRKIGRT (SEQ ID NO: 24),
RIDTACVCTLLSRTGRA (SEQ ID:25),
RIDTSCVCTLTIKRGR (SEQ ID:26),
or fragments, or variants thereof.

21. The method of claim 1 wherein neurite outgrowth is stimulated.

22. The method of claim 1 wherein neuronal cell survival is stimulated.

23. The method of claim wherein the neuronal cell is in a subject.

24. The method of claim 23 wherein the subject is suffering from a disease or other adverse medical condition.

25. The method according to claim 1 wherein said peptide sequence further comprises the amino acid motif $x^{p2}\text{-}(x^{a})\text{-}(x^{a})\text{-}x^{+/-}\text{-}x^{a2}\text{-G}$ (motif II), wherein $x^{p2}$ is a hydrophobic or basic amino acid residue,
$(X^{a})$ is any amino acid residue or a bond, $x^{+/-}$ is a charged amino acid residue, and
$x^{a2}$ is any amino acid residue.

26. The method according to claim 1 wherein said peptide sequence comprises (Motif I)-(X)$_n$-(motif II), wherein
(X)$_n$ is a bond or sequence of n consecutive amino acid residues,
n is an integer from 1 to 5, and motif II is $x^{p2}$-$(x^a)$-$(x^a)$-$x^{+/-}$-$x^{a2}$-G wherein
$x^{p2}$ is a hydrophobic or basic amino acid residue,
$(x^a)$ is any amino acid residue or a bond,
$x^{+/-}$ is a charged amino acid residue, and
$x^{a2}$ is any amino acid residue.

27. The method according to claim 1 wherein the peptide sequence of (1) consists of or the individual peptide sequences of the compound of (2) consist of 11 to 25 contiguous amino acid residues.

28. The method according to claim 1 wherein the peptide sequence of (1) consists of or the individual peptide sequences of the compound of (2) consist of 11 to 15 contiguous amino acid residues.

29. The method according to claim 26, wherein $x^{p2}$ is A, L, P or Y.

30. The method according to claim 26, wherein $x^{p2}$ is K.

31. The method according to claim 26, wherein $(x^a)$ is an amino acid residue selected from A, E, F, I, L, R, S, T or V.

32. The method according to claim 26, wherein at least one of the $(x^a)$ residues is a bond.

33. The method according to claim 26, wherein $x^{a2}$ is an amino acid residue selected from A, E, G, I, N, R, S or T.

34. The method according to claim 26, wherein $x^{+/-}$ is selected from D, E, K, R or H.

35. The method according to claim 20, wherein the fragment is an amino acid sequence comprising at least 10 amino acid residues of any of the sequences identified as SEQ ID NOs: 1, 3, 24, 25, or 26.

36. The method according to claim 20 wherein the variant is an amino acid sequence which has at least 60% homology to any of the sequences identified as SEQ ID NOs: 1, 3, 24, 25, or 26.

37. The method according to claim 24, wherein the condition or disease is a condition or disease of the peripheral or central nervous system.

38. The method according to claim 37, wherein the condition or disease is selected from postoperative nerve damage, traumatic nerve damage, impaired myelination of nerve fibers, postischaemic damage, nerve degeneration associated with diabetes mellitus, disorders affecting the circadian clock or neuro-muscular transmission.

39. The method according to claim 37, wherein the condition or disease is a cancer of the neural system.

40. The method according to claim 37, wherein the condition or disease is an impaired ability to learn and/or impaired memory.

41. The method according to claim 37, wherein the condition or disease is Parkinson's disease, Alzheimer's disease, Huntington's disease or dementia.

42. The method according to claim 37, wherein the condition or disease is a disorder of thought and/or mood, a neuropsychiatric disorder, a genetically related unipolar affective disorder, a delusional disorder, paraphrenia, paranoid psychosis, schizophrenia, schizotypal disorder, schizoaffective disorder, schizoaffective a bipolar or genetically related unipolar affective disorder, psychogenic psychosis, catatonia, a periodic bipolar or genetically related unipolar affective disorder, cycloid psychosis, schizoid personality disorder, paranoid personality disorder, a bipolar disorder, or a genetically related unipolar affective disorder.

43. The method according to claim 24, wherein the condition or disease is a prion disease.

* * * * *